(12) United States Patent
Fensome et al.

(10) Patent No.: US 7,317,037 B2
(45) Date of Patent: Jan. 8, 2008

(54) PROGESTERONE RECEPTOR MODULATORS COMPRISING PYRROLE-OXINDOLE DERIVATIVES AND USES THEREOF

(75) Inventors: Andrew Fensome, Wayne, PA (US); Casey Cameron McComas, Phoenixville, PA (US); Edward George Melenski, Collegeville, PA (US); Michael Anthony Marella, Limerick, PA (US); Jay Edward Wrobel, Lawrenceville, NJ (US); Gary Sondermann Grubb, Newtown Square, PA (US)

(73) Assignee: Wyeth, Madison, NJ (US)

( * ) Notice: Subject to any disclaimer, the term of this patent is extended or adjusted under 35 U.S.C. 154(b) by 29 days.

(21) Appl. No.: 11/175,824

(22) Filed: Jul. 6, 2005

(65) Prior Publication Data

US 2006/0030717 A1 Feb. 9, 2006

Related U.S. Application Data

(60) Provisional application No. 60/671,684, filed on Apr. 15, 2005, provisional application No. 60/600,031, filed on Aug. 9, 2004.

(51) Int. Cl.
*C07D 209/30* (2006.01)
*A61K 31/404* (2006.01)

(52) U.S. Cl. .................... 514/414; 548/411; 548/466; 206/569; 206/570

(58) Field of Classification Search ............... 548/411, 548/466; 514/414; 206/569, 570
See application file for complete search history.

(56) References Cited

U.S. PATENT DOCUMENTS

| | | | |
|---|---|---|---|
| 5,585,378 A | 12/1996 | Boar et al. | |
| 6,391,907 B1 | 5/2002 | Fensome et al. | |
| 6,407,101 B1 | 6/2002 | Collins et al. | |
| 6,444,668 B1 | 9/2002 | Grubb et al. | |
| 6,462,032 B1 | 10/2002 | Grubb et al. | |
| 6,503,937 B1 | 1/2003 | Nesvadba et al. | |
| 6,509,334 B1 | 1/2003 | Zhang et al. | |
| 6,521,657 B2 | 2/2003 | Fensome et al. | |
| 6,544,970 B2 | 4/2003 | Grubb et al. | |
| 6,562,857 B2 | 5/2003 | Collins et al. | |
| 6,566,358 B2 | 5/2003 | Zhang et al. | |
| 6,608,068 B2 | 8/2003 | Fensome et al. | |
| 6,436,929 B1 | 3/2004 | Zhang et al. | |
| 6,713,478 B2 | 3/2004 | Zhang et al. | |
| 6,759,408 B2 | 7/2004 | Grubb et al. | |
| 7,084,168 B2 | 8/2006 | Fensome et al. | |
| 2002/0128208 A1 | 9/2002 | Snyder et al. | |
| 2003/0092711 A1 | 5/2003 | Zhang et al. | |
| 2003/0158182 A1 | 8/2003 | Collins et al. | |
| 2003/0216432 A1 | 11/2003 | Pfahl et al. | |
| 2004/0002535 A1 | 1/2004 | Fensome et al. | |
| 2004/0006122 A1 | 1/2004 | Fensome et al. | |
| 2004/0034004 A1 | 2/2004 | Pfahl et al. | |
| 2004/0142933 A1 | 7/2004 | Forest et al. | |
| 2004/0152719 A1 | 8/2004 | He et al. | |
| 2004/0152755 A1 | 8/2004 | He et al. | |
| 2004/0186101 A1 | 9/2004 | Zhang et al. | |
| 2005/0227971 A1 | 10/2005 | Wilk et al. | |
| 2005/0228178 A1 | 10/2005 | Lerestif et al. | |
| 2005/0250766 A1 | 11/2005 | Wilk et al. | |
| 2005/0256110 A1 | 11/2005 | Collins et al. | |
| 2005/0261327 A1 | 11/2005 | Bock et al. | |
| 2005/0272702 A1 | 12/2005 | Wilk et al. | |
| 2006/0030615 A1 | 2/2006 | Fensome et al. | |
| 2006/0142348 A1 | 6/2006 | Singh et al. | |
| 2006/0160882 A1 | 7/2006 | Fensome et al. | |

FOREIGN PATENT DOCUMENTS

| | | |
|---|---|---|
| WO | WO-94/29272 | 12/1994 |
| WO | WO 00/66556 | 11/2000 |
| WO | WO 00/66581 | 11/2000 |
| WO | WO 200066167 A1 * | 11/2000 |
| WO | WO-03/082265 | 10/2003 |
| WO | WO-20040937247 | 5/2004 |

OTHER PUBLICATIONS

Winneker et al., "Nonsteroidal Progesterone Receptor Modulators: Structure Activity Relationships", Seminars in Reproductive Medicine, 23(1): 46 (Feb. 2005).
Collins et al., "Novel Pyrrole-Containing Progesterone Receptor Modulators", Bioorganic & Medicinal Chemistry Letters, 14: 2185 (May 3, 2004).
Fensome et al., "New Progesterone Receptor Antagonists: 3,3-Disubstituted-5-aryloxindoles", Bioorganic & Medicinal Chemistry Letters, 12: 3487 (Dec. 2, 2002).
Allan et al., "Non-steroidal Progesterone Receptor Specific Ligands", Mini-Reviews in Medicinal Chemistry, 5:701 (Aug. 2005).
Fensome et al., "Novel 5-aryl-1,3-dihydro-indole-2-thiones: Potent, Orally Active Progesterone Receptor Agonists", Bioorg. & Med. Chem. Lett., 13(7):1317-1320 (Apr. 7, 2003).
Jiang et al., "Design, Synthesis & Biological Evaluation of Novel Oxindoles as HIV-1 Non-Nucleoside Reverse Transcriptase Inhibitors. Part I", Bioorg. & Med. Chem. Lett., 16(8):2105-2108 (Feb. 9, 2006).
Terefenko et al., "SAR Studies of 6-Aryl-1,3-dihydrobenzimidazol-2-ones as Progesterone Receptor Antagonists" Bioorg. & Med. Chem. Lett., 15(15):3600-3603 (Jun. 22, 2005).

* cited by examiner

*Primary Examiner*—Rebecca Anderson
*Assistant Examiner*—Michael P. Barker
(74) *Attorney, Agent, or Firm*—Howson & Howson LLP; Arnold S. Milowsky

(57) ABSTRACT

Pyrrole-oxindole derivatives useful as progesterone receptor antagonists, and methods for preparing the same, are provided. Pharmaceutical compositions containing these derivatives are described, as is the use thereof in contraception and hormone-related conditions.

37 Claims, No Drawings

PROGESTERONE RECEPTOR MODULATORS COMPRISING PYRROLE-OXINDOLE DERIVATIVES AND USES THEREOF

CROSS-REFERENCE TO RELATED APPLICATIONS

This application claims the benefit of the priorities of U.S. Provisional Patent Application No. 60/671,684, filed Apr. 15, 2005 and U.S. Provisional Patent Application No. 60/600,031, filed Aug. 9, 2004.

BACKGROUND OF THE INVENTION

Progesterone receptor (PR) agonists and antagonists, also termed PR modulators, have been described for use in contraception and a variety of other indications.

U.S. Pat. No. 6,562,857 describes compounds that are PR agonists. The genus is characterized by compounds of the formula:

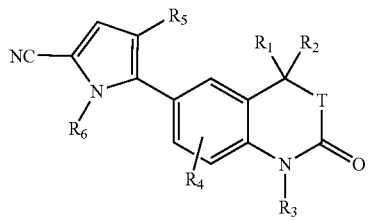

in which T is O, or absent; $R_1$ and $R_2$ are each, independently, hydrogen, alkyl, or substituted alkyl; or $R_1$ and $R_2$ are taken together to form a ring and together contain —$CH_2$(CH$_2$)$_n$CH$_2$—; n is 1 to 5; $R_3$ is hydrogen; $R_4$ is hydrogen or halogen; $R_5$ is hydrogen or alkyl; $R_6$ is hydrogen or alkyl; or a pharmaceutically acceptable salt thereof.

What are needed are novel PR modulators useful as contraceptives without the requirement for a progestin agonist or estrogen agonist.

SUMMARY OF THE INVENTION

In one aspect, the present invention provides PR modulators.

In another aspect, the present invention provides a compound of formula I, where $R_1$ to $R_9$ are defined below.

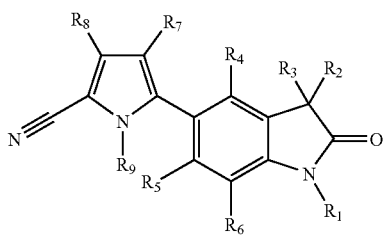

In another aspect, the present invention provides methods of preparing the compounds of the invention.

In a further aspect, the present invention provides pharmaceutical compositions containing the compounds of the invention.

In still another aspect, the present invention provides uses of the compounds of the invention for hormone replacement therapy, for synchronizing estrus, and for treating contraception, hormone neoplastic disease, dysmenorrheal, dysfunctional uterine bleeding, the symptoms of premenstrual syndrome and premenstrual dysphoric disorder, and for inducing amenorrhea.

In yet a further aspect, the present invention provides kits containing the compounds of the invention.

Other aspects and advantages of the present invention are described further in the following detailed description of the preferred embodiments thereof.

DETAILED DESCRIPTION OF THE INVENTION

The compounds prepared according to the invention are progesterone receptor (PR) antagonists, which have utility in a variety of applications. When utilized for contraception, the PR antagonist may be administered in a regimen without co-administration, i.e., in the absence of, a progestin agonist or estrogen agonist. Thus, the present invention provides regimens free of the side effects of progestin agonists or estrogen agonists. Alternatively, the PR antagonist may be administered in a regiment with co-administration of agents such as progestin agonists or estrogen agonists.

The present invention provides compounds of formula I:

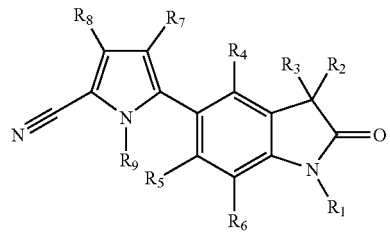

where, $R_1$ is hydrogen, alkyl, substituted alkyl, cycloalkyl, substituted cycloalkyl, $C_3$ to $C_6$ alkenyl, substituted $C_3$ to $C_6$ alkenyl, $C_3$ to $C_6$ alkynyl, or substituted $C_3$ to $C_6$ alkenyl; $R_2$ and $R_3$ are independently selected from among hydrogen, alkyl or substituted alkyl; or $R_2$ and $R_3$ are taken together to form a ring and together contain —$CH_2$—(CH$_2$)$_n$—$CH_2$— where n is 0 (i.e., a chemical bond), 1, 2, or 3; $R_4$ is hydrogen or halogen; $R_5$ is hydrogen; $R_6$ is hydrogen or halogen; $R_7$ is hydrogen, alkyl, substituted alkyl, or halogen; $R_8$ is hydrogen; $R_9$ is hydrogen, alkyl, substituted alkyl, or COOR$^A$; and R$^A$ is alkyl or substituted alkyl; or a pharmaceutically acceptable salt, a prodrug, or a tautomer thereof.

The present invention also provides compounds of formula I:

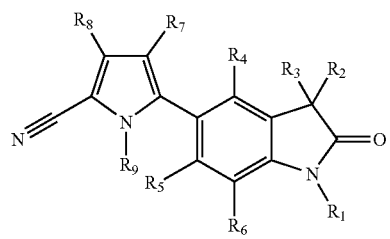

where, $R_1$ is hydrogen, alkyl, substituted alkyl, cycloalkyl, $C_3$ to $C_6$ alkenyl, or $C_3$ to $C_6$ alkynyl; $R_2$ and $R_3$ are independently selected from among hydrogen, alkyl or substituted alkyl; or $R_2$ and $R_3$ are taken together to form a ring and together contain —$CH_2$—$(CH_2)_n$—$CH_2$— where n is 0 (i.e., a chemical bond), 1, 2, or 3; $R_4$ is hydrogen or halogen; $R_5$ is hydrogen; $R_6$ is hydrogen or halogen; $R_7$ is hydrogen, alkyl, or halogen; $R_8$ is hydrogen; $R_9$ is hydrogen, alkyl, substituted alkyl, or $COOR^4$; and $R^4$ is alkyl or substituted alkyl; or a pharmaceutically acceptable salt, a prodrug, or a tautomer thereof.

In one embodiment, $R_1$ is hydrogen or alkyl and $R_2$ and $R_3$ are taken together to form a ring and together contain —$CH_2$—$(CH_2)_n$—$CH_2$— where n is 1 or 2. In another embodiment, $R_2$ or $R_3$, or both, are $C_1$ to $C_6$ alkyl. For example, either $R_2$ or $R_3$, or both, can be ethyl. In another example, $R_2$ or $R_3$, or both, are methyl. In another embodiment, $R_9$ is a substituted or unsubstituted $C_1$ to $C_6$ alkyl. For example, $R_9$ can be methyl or ethyl. In another example, $R_9$ is $C_1$ to $C_2$ substituted with a phenyl. In still another embodiment, $R_9$ is $COOR^4$. In one example, $R^4$ is tert-butyl.

Desirably, where the structure contains a halogen, the halogen is a F. However, other halogens, e.g., Cl, I or Br, may be selected. In one embodiment, $R_6$ is F. In another embodiment, $R_4$ is F.

Desirably, where $R_1$ and/or $R_9$ are substituted alkyl, the alkyl is substituted with a halogen, nitrile or benzene ring. In one embodiment, where $R_1$ is a cycloalkyl, it is $C_3$ to $C_6$ cycloalkyl.

It is desirable that at least one of $R_4$ and $R_6$ is halogen, and more desirably fluorine. Desirably, $R_6$ is halogen, and more desirably fluorine. $R_1$ is desirably hydrogen, $C_1$ to $C_6$ alkyl, $C_3$ to $C_6$ cycloalkyl, or $C_3$ to $C_6$ alkenyl, more desirably hydrogen, $C_1$ to $C_4$ alkyl, allyl, or cyclopentyl, even more desirably hydrogen or allyl, and most desirably hydrogen. $R_2$ and $R_3$ are desirably independently selected from hydrogen and $C_1$ to $C_6$ alkyl, more desirably selected from hydrogen and $C_1$ to $C_4$ alkyl, and most desirably independently selected from among hydrogen, methyl, and ethyl. Alternatively, $R_2$ and $R_3$ represent —$CH_2$—$(CH_2)_n$—$CH_2$— where n is desirably 0, 1 or 2, and more desirably is 1 or 2. $R_7$ is desirably hydrogen, halogen or $C_1$ to $C_6$ alkyl; more desirably hydrogen or $C_1$ to $C_4$ alkyl, and most desirably hydrogen. $R_9$ is desirably $C_1$ to $C_6$ alkyl, more desirably $C_1$ to $C_4$ alkyl, and most desirably methyl.

The compounds utilized according to the present invention can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups having about 1 to about 8 carbon atoms, and desirably about 1 to about 6 carbon atoms (i.e., $C_1$, $C_2$, $C_3$, $C_4$, $C_5$ or $C_6$).

The term "alkenyl" is used herein to refer to both straight- and branched-chain alkyl groups having one or more carbon-carbon double bonds and containing about 3 to about 8 carbon atoms. Desirably, the term alkenyl refers to an alkyl group having 1 or 2 carbon-carbon double bonds and having 3 to about 6 carbon atoms.

The term "alkynyl" group is used herein to refer to both straight- and branched-chain alkyl groups having one or more carbon-carbon triple bond and having 3 to about 8 carbon atoms. Desirably, the term alkynyl refers to an alkyl group having 1 or 2 carbon-carbon triple bonds and having 3 to about 6 carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, $NO_2$, amino, aryl, heterocyclic groups, aryl, alkoxy, aryloxy, alkyloxy, alkylcarbonyl, alkylcarboxy, amino, and arylthio which groups can be optionally substituted.

The term "acyl" as used herein refers to a carbonyl substituent, i.e., a C(O)(R) group where R is a straight- or branched-chain saturated aliphatic hydrocarbon group including, without limitation, alkyl, alkenyl, and alkynyl groups. Desirably, the R groups have 1 to about 8 carbon atoms, and more desirably 1 to about 6 carbon atoms. The term "substituted acyl" refers to an acyl group which is substituted with 1 or more groups including halogen, CN, OH, and $NO_2$.

The term "aryl" as used herein refers to an aromatic system which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Desirably, a substituted aryl group is substituted with 1 to about 4 substituents.

The term "heterocyclic" as used herein refers to a stable 4- to 7-membered monocyclic or multicyclic heterocyclic ring which is saturated, partially unsaturated, or wholly unsaturated. The heterocyclic ring has in its backbone carbon atoms and one or more heteroatoms including nitrogen, oxygen, and sulfur atoms. Desirably, the heterocyclic ring has about 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Desirably, a substituted heterocyclic group has 1 to 4 substituents.

The term "arylthio" as used herein refers to the S(aryl) group, where the point of attachment is through the sulfur-atom and the aryl group can be optionally substituted. The term "alkoxy" as used herein refers to the O(alkyl) group, where the point of attachment is through the oxygen-atom and the alkyl group is optionally substituted. The term "aryloxy" as used herein refers to the O(aryl) group, where the point of attachment is through the oxygen-atom and the aryl group is optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The compounds of the present invention encompass tautomeric forms of the structures provided herein characterized by the bioactivity of the drawn structures. Further, the compounds of the present invention can be used in the form of salts derived from pharmaceutically or physiologically acceptable acids, bases, alkali metals and alkaline earth metals.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts, for example, sodium, lithium, or potassium, and organic bases, such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts in the form of esters, and carbamates. Other conventional "pro-drug" forms can also be utilized which, when delivered in such form, convert to the active moiety in vivo.

These salts, as well as other compounds of the invention can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

As described herein, the compounds of formula I and/or salts, prodrugs or tautomers thereof, are delivered in regimens for contraception, therapeutic or prophylactic purposes, as described herein.

The compounds discussed herein also encompass "metabolites" which are unique products formed by processing the compounds of the invention by the cell or patient. Desirably, metabolites are formed in vivo.

The compounds of this invention are readily prepared by one of skill in the art according to the following schemes from commercially available starting materials or starting materials which can be prepared using literature procedures. These schemes show the preparation of representative compounds of this invention. Variations on these methods, or other methods known in the art can be readily utilized by one of skill in the art given the information provided herein.

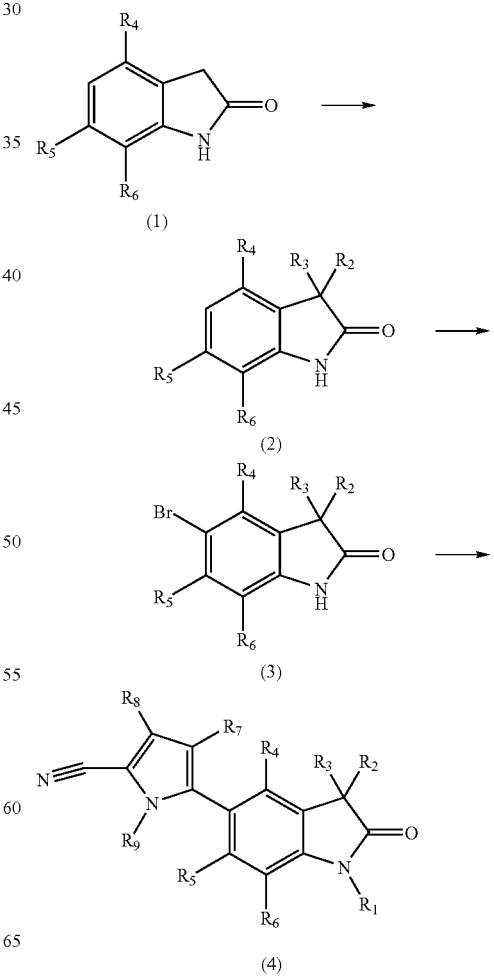

-continued

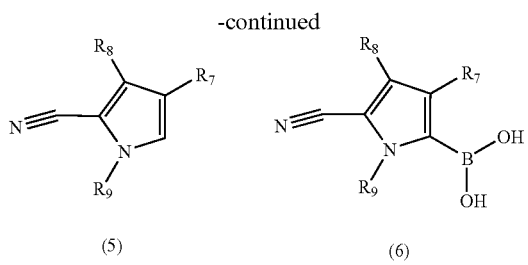

(5)            (6)

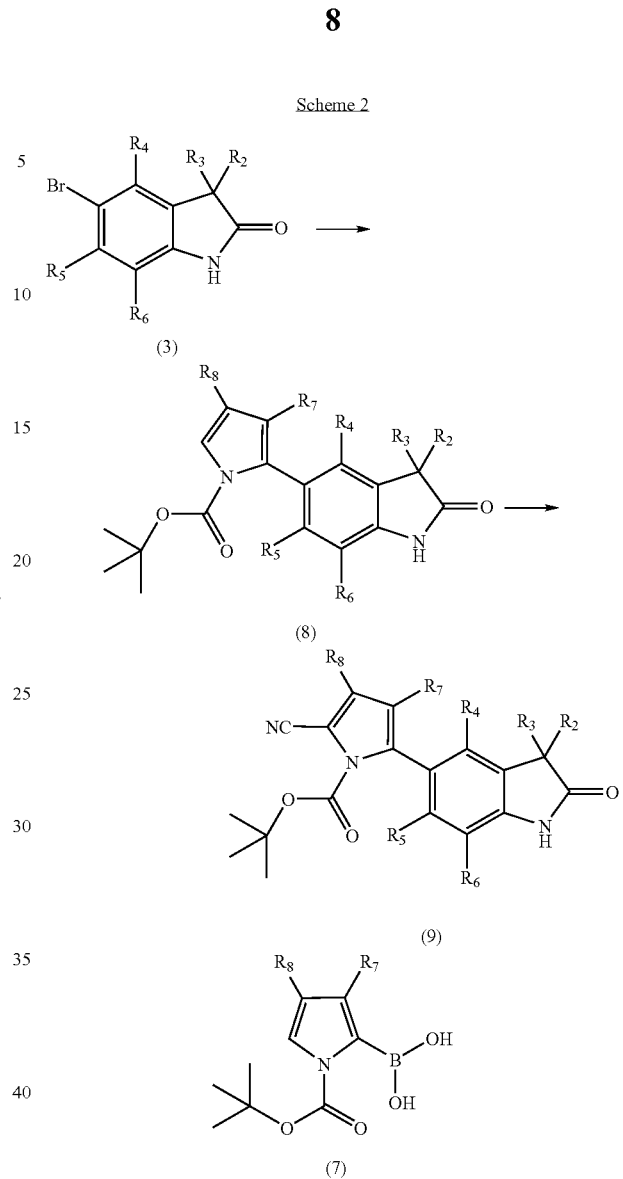

Scheme 2

According to scheme 1, an appropriately substituted oxindole (1) is treated with a suitable base (normally 2 or more molar equivalents) and an alkylating agent to afford 3,3-substituted oxindoles (2). The range of suitable bases includes alkyl lithium bases, potassium tertiary butoxide, sodium hexamethyldisilazide and similar bases. The base may also be used in conjunction with an additive. Generally the compounds of the invention are prepared using n-butyl lithium as the base in anhydrous THF in the presence of lithium chloride. The alkylating agent is normally an alkyl halide (e.g., bromide or iodide) but could also be a triflate, tosylate or mesylate. If one equivalent of alkylating agent is used then the resultant oxindole will be mono-substituted. With two equivalents, then the oxindole will be di-substituted. If the alkylating agent is bifunctional (e.g., a halide or other leaving group at both ends of an alkyl chain) then a spirocyclic ring is produced.

3,3-substituted oxindoles (2) are then brominated to give the bromide compound (3). The bromination is conveniently carried out with bromine in a solvent such as methylene chloride or acetic acid, which may be buffered with an additive such as sodium acetate. The bromination may also be accomplished with N-bromosuccinimide or pyridinium bromide per bromide. The bromide compound (3) is then converted into compound (4) under the action of a palladium catalyst and a suitable coupling partner. The coupling partner may be formed in situ from the pyrrole (5) and lithium di-isopropylamide and a trialkyl borate or may be the pre-formed boronic acid (6). The source of palladium is normally tetrakis(triphenylphosphine)palladium (0) or another suitable source such as palladium dibenzylidene acetone in the presence of tributylphosphine (Fu, G. C. et al. Journal of the *American Chemical Society*, 2000, 122, 4020, for alternate catalyst systems see also Hartwig, J. F. et al. *Journal of Organic Chemistry*, 2002, 67, 5553). A base is also required in the reaction, the normal choices are sodium or potassium carbonate, cesium fluoride, potassium fluoride, potassium phosphate or a tertiary amine base such as triethylamine, but others are also available. The choice of solvents includes THF, dimethoxyethane, dioxane, ethanol, water, and toluene amongst others. Depending on the reactivity of the coupling partners and reagents, the reaction may be conducted up to the boiling point of the solvents, or may indeed be accelerated under microwave irradiation, if necessary.

When $R_1$ is to be a substituted alkyl group, then compound (4), when $R_1$ is H, is treated with a suitable base (for example sodium hydride, potassium tert-butoxide or cesium carbonate) in a solvent such as THF or DMF, followed by treatment with the appropriate alkylating agent. The alkylating agent would normally be an alkyl halide, or an alkyl sulfonate (tosylate, mesylate or triflate for example).

An alternative strategy may be used to prepare compound (4) when $R_9$=hydrogen. This strategy entails coupling bromide (3) with a pyrrole boronic acid of formula (7) under conditions as described above. Compound (8) may then be converted into the nitrile (9). This is most conveniently accomplished by the action of chlorosulfonylisocyanate followed by treatment with DMF, although other methods are also available. The t-butylcarbonate protecting group is then removed to afford the product (4), $R_9$=H. See, scheme 2

Where the oxindole (1) is not commercially available, it may be prepared according to scheme 3. As an example, 2,6-difluoroaniline (10) is oxidized to give compound (11) under the action of an oxidant such as sodium perborate in acetic acid. Compound (11) is then converted into compound (12) by the addition of a dialkyl (normally dimethyl or diethyl) malonate in the presence of a base (sodium hydride or alkyl carbonate) in a suitable solvent, normally DMF. Compound (12) is then hydrolyzed and de-carboxylated to give compound (13) by treatment with strong aqueous acid (hydrochloric acid). Compound (13) is then reduced (hydrogen gas and a transition metal catalyst such as palladium on carbon or by a dissolving metal reduction such as tin, zinc or iron in hydrochloric or acetic acid). The product recovered is the oxindole (14). If the conditions are mild, an intermediate carboxylic acid (15) is sometimes isolated. In this case the ring may be closed under treatment with para-toluene sulfonic acid in boiling ethanol.

Alternatively, compounds (1) to (3) can be prepared according to the routes described in U.S. Provisional Patent Application Nos. 60/676,149 and 60/676,381, which are hereby incorporated by reference in their entirety.

This procedure is also effective for other substitution patterns, given a correctly substituted starting material (10).

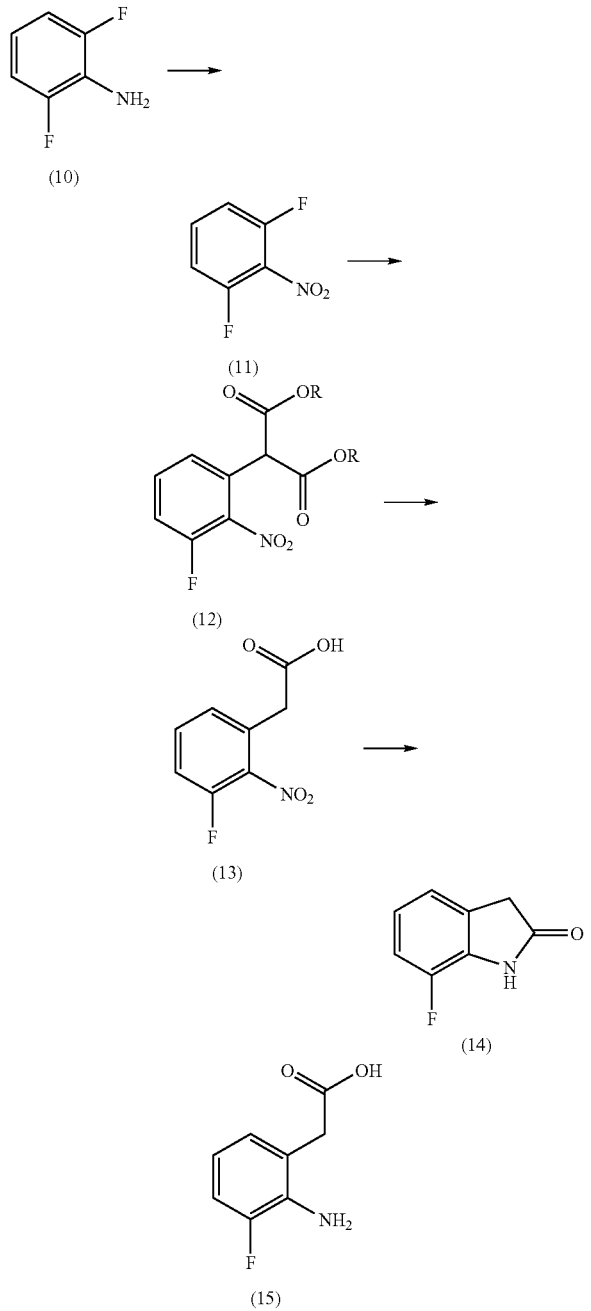

In one embodiment, the methods of the present invention are prepared by (a) alkylating an optionally substituted oxindole; (b) brominating the product of step (a); and (c) coupling the product of step (b) with a 2-cyanopyrrole. The optionally substituted oxindole is of the structure, where $R_4$ to $R_6$ are described above.

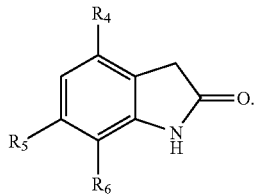

The product of step (a) is of the structure, where $R_2$ to $R_6$ are defined above.

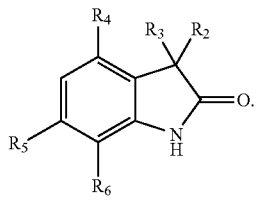

The product of step (b) is typically of the structure, where $R_2$ to $R_6$ are defined above:

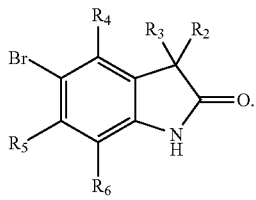

The cyanopyrrole utilized to prepare the 3,3-substituted oxindoles are of the structure, where $R_7$ to $R_9$ are defined above.

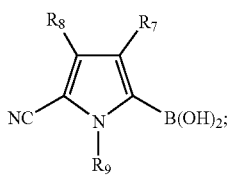

Alternatively, the cyanopyrrole is prepared by reacting lithium diisopropylamide, a tri-alkylborate, and a pyrrole of the following structure, where $R_7$ to $R_9$ are defined below.

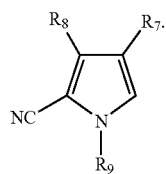

In another embodiment, one method for preparing a compound of the present invention includes (a) coupling a 5-bromo substituted oxindole and a pyrrole boronic acid containing a protecting group; (b) converting the product of step a) to the nitrile; and (c) removing said protecting group from the product of step b). The pyrrole boronic acid is optionally of the structure, where $R_7$ and $R_8$ are defined above.

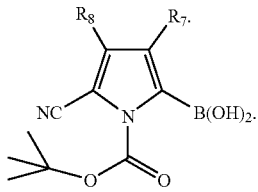

Further, the product of step (b) is of the structure, where $R_2$ to $R_8$ are defined below.

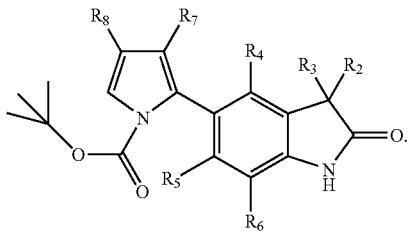

In a further embodiment, the present invention provides a method for preparing compound of the invention include (a) alkylating an optionally substituted oxindole of the structure, where $R_4$ to $R_6$ are defined above.

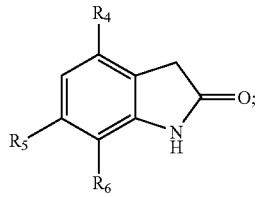

(b) brominating the product of step a) to form a compound of the structure, where $R_2$ to $R_6$ are defined above.

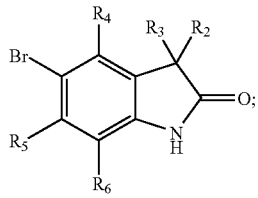

(c) coupling the product of step b) with a 2-cyanopyrrole of the structure, where $R_7$ to $R_9$ are defined above.

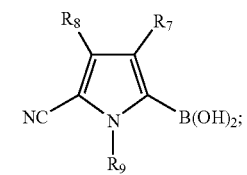

Alternatively, the product of step b) is coupled with a 2-cyanopyrrole cyanopyrrole which is the product of the reaction of lithium diisopropylamide, a tri-alkylborate, and a pyrrole of the following structure, where $R_7$ to $R_9$ are defined above.

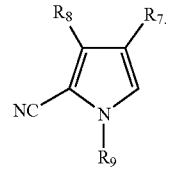

This invention includes pharmaceutical compositions comprising one or more compounds of this invention and a pharmaceutically acceptable carrier or excipient. The invention also includes methods of treatment which comprise administering to a mammal a pharmaceutically effective amount of one or more compounds as described above as antagonists of the progesterone receptor.

The compounds of this invention can be utilized in methods of contraception, hormone replacement therapy and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors; dysmenorrhea; dysfunctional uterine bleeding; and symptoms of premenstrual syndrome and premenstrual dysphoric disorder; and for inducing amenorrhea. Additional uses of the present progesterone receptor antagonists include the synchronization of the estrus in livestock.

Suitably, the PR antagonists used in the invention are formulated for delivery by any suitable route including, e.g., transdermal, mucosal (intranasal, buccal, vaginal), oral, parenteral, etc, by any suitable delivery device including, e.g., transdermal patches, topical creams or gels, a vaginal ring, among others.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, desirably given in divided doses one to four times a day, or in a sustained release form. For most large mammals, the total daily dosage is from about 1 to 100 mg, desirably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The pharmaceutical compositions from the standpoint of ease of preparation and administration are solid compositions, particularly tablets and hard-filled or liquid-filled capsules. Oral administration of the compounds is desirable. These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

In one embodiment, the present invention provides cyclic regimens involving administration of a PR antagonist of the invention alone. In another embodiment, the cyclic regimen involves administration of a PR antagonist of the invention in combination with an estrogen or progestin, or both. Particularly desirable progestins can be selected from among those described in U.S. Pat. Nos. 6,355,648; 6,521,657; 6,436,929; 6,540,710; and 6,562,857 and U.S. Patent Application Publication No. 2004-0006060-A1. Still other progestins are known in the art and can be readily selected. In one embodiment, the present invention provides combination regimens with the PR agonist (i.e., progestin) tanaproget 5-(4,4-dimethyl-2-thioxo-1,4-dihydro-2H-3,1-benzoxazin-6-yl)-1-methyl-1H-pyrrole-2-carbonitrile.

This invention further includes administration regimens carried out over 28 consecutive days. These regimens may be continuous, or may involve a terminal portion of the cycle, e.g., 0 to 7 days, containing administration of no progestins, estrogens or anti-progestins. See, e.g., the regimens described in U.S. Provisional Patent Application Nos. 60/585,883 and 60/676,135, which are hereby incorporated by reference.

The regimens described herein may be utilized for contraception, or for any of the other indications described herein. Where administration is for contraception, the compositions may be formulated in oral dosage units.

When utilized for contraception, the PR antagonists of the invention may be administered to a female of child bearing age, alone or in combination with an estrogen. For the first 14 to 24 days of the cycle, a progestational agent is administered, desirably at a dosage range equal in progestational activity to about 35 μg to about 150 μg levonorgestrel per day, and more desirably equal in activity to about 35 μg to about 100 μg levonorgestrel per day. A PR antagonist may then be administered alone or in combination with an estrogen for a period of 1 to 11 days to begin on any cycle day between day 14 and 24. The antiprogestin in these combinations may be administered at a dose of from about 2 μg to about 50 μg per day and the estrogen may be administered at a dose of from about 10 μg to about 35 μg per day. In an oral administration, a package or kit containing 28 tablets will include a placebo tablet on those days when the PR antagonist of the invention or progestin or estrogen is not administered.

In one embodiment of this invention, the compounds of this invention may be administered alone or in combination with estrogen for the initial 18 to 21 days of a 28-day cycle, followed by administration of a compound of the invention, alone or in combination with an estrogen, for from 1 to 7 days. The estrogen to be used in the combinations and formulations of this invention is desirably ethinyl estradiol.

Progestational agents useful with this invention include, but are not limited to, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Among the desirable progestins for use in the combinations of this invention are levonorgestrel, gestodene and trimegestone.

Examples of orally administered regimens of this invention over a 28 day cycle include administration of progestational agent solely for the first 21 days at a daily dose equal in progestational activity to from about 35 to about 100 μg of levonorgestrel. A PR antagonist compound of this invention can then be administered at a daily dose of from about 2 to 50 mg from day 22 to day 24, followed by no administration or administration of a placebo for days 25 to 28. It is most desirable that the daily dosages of each relevant active ingredient be incorporated into a combined, single daily dosage unit, totaling 28 daily units per 28-day cycle.

In another regimen, a progestational agent may be coadministered for the first 21 days at a daily dose equal in progestational activity to from about 35 to about 150 μg levonorgestrel, desirably equal in activity to from about 35 to about 100 μg levonorgestrel, with an estrogen, such as ethinyl estradiol, at a daily dose range of from about 10 to about 35 μg. This may be followed as described above with a PR antagonist of the invention administered at a daily dose of from about 2 to 50 mg from day 22 to day 24, followed by no administration or administration of a placebo for days 25 to 28.

Still another regimen within the scope of this invention will include coadministration from days 1 to 21 of a progestational agent, e.g., levonorgestrel, being administered at a daily dose equal in progestational activity to from about 35 to about 100 μg levonorgestrel, and an estrogen, such as ethinyl estradiol, at a daily dose range of from about 10 to about 35 μg. This will be followed on days 22 to 24 by coadministration of a PR antagonist of the invention (2 to 50 mg/day) and an estrogen, such as ethinyl estradiol, at a daily dose of from about 10 to about 35 µg. From day 25 to day 28, this regimen may be followed by no administration or administration of a placebo.

This invention also includes kits or packages of pharmaceutical formulations designed for use in the regimens described herein. These kits are desirably designed for daily oral administration over a 28-day cycle, desirably for one oral administration per day, and organized so as to indicate a single oral formulation or combination of oral formulations to be taken on each day of the 28-day cycle. Desirably, each kit will include oral tablets to be taken on each the days specified, desirably one oral tablet will contain each of the combined daily dosages indicated.

According to the regimens described above, one 28-day kit may comprise (a) an initial phase of from 14 to 21 daily dosage units of a progestational agent equal in progestational activity to about 35 to about 150 µg levonorgestrel, desirably equal in progestational activity to about 35 to about 100 µg levonorgestrel; (b) a second phase of from 1 to 11 daily dosage units of a PR antagonist compound of this invention, each daily dosage unit containing an antiprogestin compound at a daily dosage of from about 2 to 50 mg; and (c) optionally, a third phase of an orally and pharmaceutically acceptable placebo for the remaining days of the cycle in which no antiprogestin, progestin or estrogen is administered.

In one embodiment of this kit, the initial phase involves 21 daily dosage units as described in the preceding passage, a second phase of 3 daily dosage units for days 22 to 24 of a PR antagonist compound of this invention and an optional third phase of 4 daily units of an orally and pharmaceutically acceptable placebo for each of days 25 to 28.

In another embodiment, a 28-day cycle packaging regimen or kit of this invention contains, a first phase of from 18 to 21 daily dosage units, and more desirably, 21 days, as described in the preceding passages, and, further including, as an estrogen, ethinyl estradiol at a daily dose range of from about 10 to about 35 µg; a second phase of from 1 to 7 daily dosage units, and desirably, 4 daily dosage units, as described above, and an optional placebo for each of the remaining 0-9 days, or about 4 days, in the 28-day cycle in which no progestational agent, estrogen or antiprogestin is administered.

A further 28-day packaged regimen or kit of this invention comprises (a) a first phase of from 18 to 21 daily dosage units, each containing a progestational agent of this invention at a daily dose equal in progestational activity to about 35 to about 150 µg levonorgestrel, desirably equal in activity to from about 35 to about 100 µg levonorgestrel, and ethinyl estradiol at a daily dose range of from about 10 to about 35 µg; (b) a second phase of from 1 to 7 daily dose units, each daily dose unit containing an antiprogestin of this invention at a concentration of from 2 to 50 mg and ethinyl estradiol at a concentration of from about 10 to about 35 µg; and (c) optionally, an orally and pharmaceutically acceptable placebo for each of the remaining 0-9 days in the 28-day cycle in which no progestational agent, estrogen or antiprogestin is administered.

In one embodiment, the package or kit just described comprises a first phase of 21 daily dosage units; a second phase of 3 daily dose units for days 22 to 24, each dose unit containing an antiprogestin of this invention at a concentration of from 2 to 50 mg and ethinyl estradiol at a concentration of from about 10 to about 35 µg; and optionally, a third phase of 4 daily units of an orally and pharmaceutically acceptable placebo for each of days 25 to 28.

In each of the regimens and kits just described, it is desirable that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also desirable that the kits contain the placebo described for the final days of the cycle. It is further desirable that each package or kit comprise a pharmaceutically acceptable package having indicators for each day of the 28-day cycle, such as a labeled blister package or dial dispenser packages known in the art.

As used herein, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

The desirable pharmaceutical compositions from the standpoint of ease of preparation and administration are solid compositions, particularly tablets and hard-filled or liquid-filled capsules. Oral administration of the compounds is desirable.

These active compounds may also be administered via a vaginal ring. Suitably, use of the vaginal ring is timed to the 28 day cycle. In one embodiment, the ring is inserted into the vagina, and it remains in place for 3 weeks. During the fourth week, the vaginal ring is removed and menses occurs. The following week a new ring is inserted to be worn another 3 weeks until it is time for the next period. In another embodiment, the vaginal ring is inserted weekly, and is replaced for three consecutive weeks. Then, following one week without the ring, a new ring is inserted to begin a new regimen. In yet another embodiment, the vaginal ring is inserted for longer or shorter periods of time.

For use in the vaginal ring, a PR antagonist compound is formulated in a manner similar to that described for contraceptive compounds previously described for delivery via a vaginal ring. See, e.g., U.S. Pat. Nos. 5,972,372; 6,126,958 and 6,125,850.

In still another aspect of the invention, the PR antagonist compound(s) are delivered via a transdermal patch. Suitably, use of the patch is timed to the 28 day cycle. In one embodiment, the patch is applied via a suitable adhesive on the skin, where it remains in place for 1 week and is replaced weekly for a total period of three weeks. During the fourth week, no patch is applied and menses occurs. The following week a new patch is applied to be worn to begin a new regimen. In yet another embodiment, the patch remains in place for longer, or shorter periods of time.

The invention further provides a kits and delivery devices containing the compounds of the invention for a variety of other therapeutic uses as described herein including, e.g., hormone replacement therapy, the treatment and/or prevention of benign and malignant neoplastic disease. Such kits contain components in addition to the compounds of the invention, including, e.g., instructions for delivery of the compounds of the invention, diluents, vials, syringes, packaging, among other items. Such kits may optionally be adapted for the selected application, e.g., hormone replacement therapy, treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors, or the synchronization of the estrus in livestock.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

5-(7-fluoro-3,3-dimethyl-2-oxo-2,3-dihydro-1H-indol-5-yl)-1-methyl-1H-pyrrole-2-carbonitrile A. 2,6-difluoronitrobenzene 2,6-Difluoroaniline (11.0 g, 85 mmol) in glacial acetic acid (50 mL) was added slowly to a stirred suspension of sodium perborate tetrahydrate (65 g, 422 mmol) in glacial acetic acid (250 mL) at 80° C. The temperature was maintained between 80-90° C. for 1 hour. The cooled reaction mixture was poured into water and extracted twice with diethyl ether, the combined organic layers were washed with a dilute solution of sodium bicarbonate, dried (MgSO$_4$) and evaporated. The residue was purified by silica gel column chromatography (Hexane:THF, 9:1) and the product washed with hexane to afford 2,6-difluoronitrobenzene (7.0 g) which was used without further examination.

B. 2-(3-Fluoro-2-nitro-phenyl)-malonic acid dimethyl ester

To a solution of 2,6-difluoronitrobenzene (5.0 g, 31.44 mmol) in dry DMF (50 mL) was added potassium carbonate (4.41 g, 32 mmol) and dimethylmalonate (3.6 mL, 31.44 mmol). The reaction mixture was heated to 65° C. and stirred for 24 hours. After cooling to room temperature, the mixture was neutralized with dilute aqueous HCl and extracted with diethyl ether, dried (MgSO$_4$), and concentrated in vacuo. Crystallization from hexane/ethylacetate (95/5), gave 2-(3-fluoro-2-nitro-phenyl)-malonic acid dimethyl ester (4.6 g, 54%).

HRMS: calc'd for $C_{11}H_{10}FNO_6$, 271.0492. found (ESI, [M+H]$^+$), 272.0576.

C. (3-Fluoro-2-nitro-phenyl)-acetic acid 2-(3-Fluoro-2-nitro-phenyl)-malonic acid dimethyl ester (12 g, 44 mmol) in 200 mL 6N hydrochloric acid (6N, 200 mL) was heated under reflux for 4 hours. The mixture was cooled, diluted with 250 mL of water and extracted with diethyl ether, dried (MgSO$_4$), and concentrated in vacu., Crystallization from hexane/ethylacetate (95/5), gave (3-fluoro-2-nitro-phenyl)-acetic acid (7.6 g, 54%) which was used without further examination.

D. 7-Fluoro-1,3-dihydro-indol-2-one (3-fluoro-2-nitro-phenyl)-acetic acid (9.6 g, 48 mmol) was dissolved in acetic acid (100 mL) and hydrogenated over 10% palladium on carbon (1.3 g), at 50 psi for 24 hours. The catalyst was removed by filtration through the Celite® reagent and the solvent was evaporated. The mixture was then dissolved in ethanol (100 mL), para-toluenesulfonic acid (50 mg) was added and the mixture heated under reflux for 1 hour. The mixture was cooled, poured into water, extracted with ethyl acetate, dried (MgSO$_4$), and evaporated. The solid was triturated with hexane/ethyl acetate (95/5) to give 7-fluoro-1,3-dihydro-indol-2-one (6 g, 83%). HRMS: calc'd for $C_8H_6FNO$, 151.0433; found (ESI, [M+H]$^+$), 152.0515

E. 7-Fluoro-3,3-dimethyl-1,3-dihydro-2H-indol-2-one

7-Fluoro-1,3-dihydro-indol-2-one (7.3 g, 48 mmol) and lithium chloride (6.67 g, 158 mmol) was dissolved in THF (200 mL). The solution was then cooled to –78° C. and n-butyllithium (2.5 M, 40 mL, 100 mmol) was added slowly over a 15 minute period. After 20 minutes at –78° C., methyl iodide (6 mL, 96 mmol) was added and the mixture allowed to warm to room temperature. After 24 hours, the mixture was poured into water and extracted with ethyl acetate, dried (MgSO$_4$), and concentrated in vacuo. Flash chromatography (SiO$_2$, Hexane/ethylacetate 9/1 then 8/2) gave 7-fluoro-3,3-dimethyl-1,3-dihydro-2H-indol-2-one (4.1 g, 48%): HRMS: calc'd for $C_{10}H_{10}FNO$, 179.0831; found (ESI, [M+H]$^+$), 180.0831

F. 5-Bromo-7-fluoro-3,3-dimethyl-1,3-dihydro-2H-indol-2-one

7-Fluoro-3,3-dimethyl-1,3-dihydro-2H-indol-2-one (4.1 g, 22.9 mmol) was dissolved in dichloromethane (100 mL) and acetic acid (2 mL) at room temperature. Bromine (1.2 mL, 23 mmol) was added and the solution allowed to stir for 24 hours. The reaction mixture was poured into sodium thiosulfate solution, extracted with diethyl ether, dried (MgSO$_4$), evaporated and the crude product triturated with hexane to give 5-bromo-7-fluoro-3,3-dimethyl-1,3-dihydro-2H-indol-2-one (4.84 g, 82%): HRMS: calc'd for $C_{10}H_9BrFNO$, 256.9852; found (ESI, [M–H]$^-$), 255.9781.

G. 5-(7-fluoro-3,3-dimethyl-2-oxo-2,3-dihydro-1H-indol-5-yl)-1-methyl-1H-pyrrole-2-carbonitrile 5-Bromo-7-fluoro-3,3-dimethyl-1,3-dihydro-indol-2-one (5.16 g, 20.0 mmol), 1-methyl-5-cyano-2-pyrroleboronic acid (5.4 g, 36 mmol), KF (3.83 g, 66 mmol), and Pd$_2$(dba)$_3$ monochloroform adduct (516 mg, 0.500 mmol) were added to a 200 mL round bottom flask under nitrogen. The flask was sealed and purged with nitrogen for 5 min. THF (50 mL) was added and the mixture was purged with nitrogen for an additional 5 min. A solution of tri-t-butylphosphine (10% wt in hexanes) (2.97 mL, 1.00 mmol) was added via syringe and the mixture was stirred vigorously at 25° C. for 5 h. The mixture was diluted with 250 mL of EtOAc, filtered through a plug of silica gel, washed through with 200 mL of EtOAc and concentrated to give a crude brown/black semi-solid. Purification by flash chromatography (20% acetone/hexane) afforded the title compound (4.5 g, 80%) as an off-white solid.

HRMS: calc'd for $C_{16}H_{14}FN_3O$, 283.1121; found (ESI, [M–H]$^-$), 282.1034

Analytical HPLC: Major=98.9% at 210-370 nm window=99.2% at 286 nm (max. abs) RT=8.7 min, 85/15-5/95 (Ammon. Form. Buff. pH=3.5/ACN+MeOH) for 10 min, hold 4 min, the Xterra® instrument RP18, 3.5 µ, 150×4.6 mm.

Example 2

5-(4-fluoro-3,3-dimethyl-2-oxo-2,3-dihydro-1H-indol-5-yl)-1-methyl-1H-pyrrole-2-carbonitrile

A. 2-(2-Fluoro-6-nitro-phenyl)-malonic acid dimethyl ester

To a solution of 2,3-difluoronitrobenzene (9 g, 56 mmol) in DMF was added potassium carbonate (13.8 g, 100 mmol) and dimethylmalonate (6.88 mL, 60 mmol). The reaction mixture was heated to 65° C. and stirred 24 hours. The mixture was cooled, neutralized with dilute HCl and extracted with diethyl ether, the organic layers were dried over magnesium sulfate, and concentrated in vacuo. The crude product was recrystallized from hexane/ethylacetate (95/5), and filtered to afford 2-(2-fluoro-6-nitro-phenyl)-malonic acid dimethyl ester (6.6 g, 43%).

B. (2-fluoro-6-nitrophenyl)acetic acid 2-(2-Fluoro-6-nitro-phenyl)-malonic acid dimethyl ester (6.5 g, 23.98 mmol) was refluxed in 200 mL 6N hydrochloric acid for 24 hours. The solid was collected by suction filtration, and dried to give 3.3 g, 54% yield of the title compound.

C. 4-fluoro-1,3-dihydro-2H-indol-2-one (2-fluoro-6-nitrophenyl)acetic acid (3.3 g, 16.6 mmol) was dissolved in acetic acid (20 mL) and hydrogenated over palladium on carbon (10%, 0.5 g) at 50 psi for 24 hours. The catalyst was removed by filtration through the Celite® reagent, which was washed with methanol, and the combined organics were then evaporated. The reaction mixture was then dissolved in ethanol (100 mL), 50 mg of para-toluenesulfonic acid was added, and the mixture heated under reflux for 1 hour. The mixture was poured into water, extracted with ethyl acetate, dried over magnesium sulfate, and evaporated. The solid was triturated with hexane/ethyl acetate (95/5) to give 1.7 g, 67% of 4-fluoro-1,3-dihydro-2H-indol-2-one: HRMS [M+H]$^+$=152.0515

D. 4-Fluoro-3,3-dimethyl-1,3-dihydro-2H-indol-2-one

4-Fluoro-1,3-dihydro-2H-indol-2-one (3.4 g, 22.5 mmol) and lithium chloride (2.7 g, 60 mmol) was dissolved in THF (100 mL). The solution was then cooled to −78° C. and n-butyllithium (7 mL, 2.5M in hexanes, 15 mmol) was added slowly over a 15 minute period. Methyl iodide (3.08 mL, 50 mmol) was added and the mixture allowed to warm up to room temperature. After 24 hours, the mixture was poured into water and extracted with ethyl acetate, dried over magnesium sulfate, and concentrated in vacuo. Flash chromatography (SiO$_2$, Hexane/ethylacetate 9/1 then 8/2) gave 4-fluoro-3,3-dimethyl-1,3-dihydro-2H-indol-2-one (1.0 g, 25%)

E. 5-Bromo-4-fluoro-3,3-dimethyl-1,3-dihydro-2H-indol-2-one

4-Fluoro-3,3-dimethyl-1,3-dihydro-2H-indol-2-one (1 g, 22.9 mmol) was dissolved in dichloromethane (DCM) (50 mL) and acetic acid (2 mL) at room temperature. Bromine (0.386 mL, 7.5 mmol) was added and the solution allowed to stir 24 hours. The reaction mixture was poured into sodium thiosulfate solution, extracted with diethyl ether, the combined organic layers were dried over magnesium sulfate and evaporated. Trituration of the crude product with hexane gave 5-bromo-4-fluoro-3,3-dimethyl-1,3-dihydro-2H-indol-2-one (1.25 g, 87%): HRMS [M−H]$^-$ 255.9781

F. 5-(4-fluoro-3,3-dimethyl-2-oxo-2,3-dihydro-1H-indol-5-yl)-1-methyl-1H-pyrrole-2-carbonitrile 5-bromo-4-fluoro-3,3-dimethyl-1,3-dihydro-2H-indol-2-one (1.25 g, 4.86 mmol) and tetrakis(triphenylphosphine)palladium(0) (0.4 g) was dissolved in ethylene glycol dimethyl ether (40 mL) and stirred 15 minutes. N-methyl-5-cyanopyrroleboronic acid (2.0 g, 13.33 mmol) and potassium carbonate (3.48, 25 mmol) were added followed by water (20 mL) and the mixture heated under reflux (24 hours). The mixture was then poured into water, neutralized with dilute hydrochloric acid, and extracted with ethylacetate. The solvent was dried over magnesium sulfate, and concentrated in vacuo. Flash chromatography; SiO$_2$, Hexane/THF 9/1 then 7/3 gave 5-(4-fluoro-3,3-dimethyl-2-oxo-2,3-dihydro-1H-indol-5-yl)-1-methyl-1H-pyrrole-2-carbonitrile (0.060 g, 5%):

HRMS: calcd for $C_{16}H_{14}FN_3O$, 283.1121; found (ESI, [M+H]$^+$), 284.1121.

Analytical HPLC: Retention time=8.8 min, purity=100% at 210-300 nm and 100% at 274 nm (max absorption), 85/15-5/95 (Ammon. Form. Buff. pH=3.5/ACN+MeOH) for 10 min, hold 4 min, the Xterra® RP18 instrument, 3.5μ, 150×4.6 mm.

Example 3

5-(7'-fluoro-2'-oxo-1',2'-dihydrospiro[cyclopropane-1,3'-indol]-5'-yl)-1-methyl-1H-pyrrole-2-carbonitrile

A. 7'-fluorospiro[cyclopropane-1,3'-indol]-2'(1'H)-one

7-Fluorooxindole (1.28 g, 8.50 mmol) and lithium chloride (0.899 g, 21.3 mmol) were suspended in 80 mL of THF and cooled to 0° C. n-Butyllithium (8.5 mL, 16.9 mmol) was added slowly, and the mixture was stirred for 20 min, and then dibromoethane (0.73 mL, 8.5 mmol) was added. The mixture was warmed to 25° C. and stirred for 16 h. The reaction was quenched with saturated aqueous NH$_4$Cl and diluted with ether. The organics were washed with water, brine, dried over MgSO$_4$, and concentrated. Flash chromatography (10% acetone/hexane) afforded 0.54 g (36%) of 7'-fluorospiro[cyclopropane-1,3'-indol]-2'(1'H)-one as a white solid: HRMS: calcd for $C_{10}H_8FNO$, 177.0590; found (ESI, [M+H]$^+$), 178.0659

Analytical HPLC: retention time 6.6 min, 210-370 nm, the Xterra® RP18 instrument, 3.5μ, 150×4.6 mm 40 C 85/15-5/95 (Ammon. Form. Buff. pH=3.5/ACN+MeOH) for 10 min, hold 4 min 1.2 mL/min 5 μL injection.

B. 5'-Bromo-7'-fluorospiro[cyclopropane-1,3'-indol]-2'(1'H)-one

7'-Fluorospiro[cyclopropane-1,3'-indol]-2'(1'H)-one (0.54 g, 3.05 mmol) was dissolved in 20 mL of CH$_2$Cl$_2$ and sodium acetate (0.28 g, 3.36 mmol) was added followed by bromine (0.173 mL, 3.36 mmol). The mixture was stirred at 25° C. for 16 h then diluted with ether and washed with Na$_2$S$_3$O$_3$, sodium bicarbonate, water, brine, dried over MgSO$_4$, and concentrated. Purification by flash chromatography (15% acetone/hexane) afforded 5'-Bromo-7'-fluorospiro[cyclopropane-1,3'-indol]-2'(1'H)-one (0.64 g, 82%) as a white solid:

Analytical HPLC: retention time 8.4 min, 210-370 nm the Xterra® RP18 instrument, 3.5μ, 150×4.6 mm 40 C 85/15-5/95 (Ammon. Form. Buff. pH=3.5/ACN+MeOH) for 10 min, hold 4 min 1.2 mL/min 5 μL injection.

C. 5-(7'-fluoro-2'-oxo-1',2'-dihydrospiro[cyclopropane-1,3'-indol]-5'-yl)-1-methyl-1H-pyrrole-2-carbonitrile 5'-Bromo-7'-fluorospiro[cyclopropane-1,3'-indol]-2'(1'H)-one (0.60 g, 2.3 mmol), 1-methyl-5-cyano-2-pyrroleboronic acid (0.63 g, 4.2 mmol), KF (0.44 g, 7.6 mmol), and $Pd_2(dba)_3$ monochloroform adduct (60 mg, 0.058 mmol) were added to a vial and then purged with nitrogen. THF (5.5 mL) was added and the mixture was purged with nitrogen for 5 min. A solution of tri-t-butylphosphine (10% wt in hexanes) (0.342 mL, 0.115 mmol) was added via syringe and the mixture was stirred vigorously at 25° C. for 2.5 h. The mixture was diluted with 100 mL of EtOAc and filtered through a plug of silica gel and concentrated. Purification by flash chromatography (25% acetone/hexane) afforded the title compound (0.53 g, 83%) as a white solid. MP 228-231° C.

Analytical HPLC: retention time 8.6 min, 210-370 nm, the Xterra® RP18 instrument, 3.5μ, 150×4.6 mm 40° C., 85/15-5/95 (Ammon. Form. Buff. pH=3.5/ACN+MeOH) for 10 min, hold 4 min 1.2 mL/min 5 μL injection.

Example 4

5-(7-Fluoro-1,3,3-trimethyl-2-oxo-2,3-dihydro-1H-indol-5-yl)-1-methyl-1H-pyrrole-2-carbonitrile A. 7-fluoro-1,3,3-trimethyl-1,3-dihydro-2H-indol-2-one 7-Fluorooxindole (1.51 g, 10 mmol) and lithium chloride (1.06 g, 25 mmol) were suspended in 30 mL of THF and cooled to 0° C. n-Butyllithium (10 mL, 20 mmol) was added slowly and the mixture was stirred for 20 min. Iodomethane (1.24 mL, 20 mmol) was added and the mixture was stirred at 0° C. for 1 hour then warmed to 25° C. and stirred for 16 h. The reaction was quenched with saturated aqueous $NH_4Cl$ and diluted with ethyl acetate. The organics were washed with water, saturated aqueous NaCl, dried over $MgSO_4$, and concentrated. Flash chromatography (5% acetone/hexane) afforded the title compound 0.12 g (7%) as a white solid.

HRMS: calcd for $C_{11}H_{12}FNO$, 193.0903; found (ESI, [M+H]$^+$), 194.0976;

B. 5-bromo-7-fluoro-1,3,3-trimethyl-1,3-dihydro-2H-indol-2-one

7-Fluoro-1,3,3-trimethyl-1,3-dihydro-2H-indol-2-one (0.10 g, 0.52 mmol) was dissolved in 5 mL of $CH_2Cl_2$ and sodium acetate (47 mg, 0.56 mmol) was added followed by bromine (0.029 mL, 0.56 mmol). The mixture was stirred at 25° C. for 16 h then loaded directly onto a silica gel column. The column was eluted with 250 mL of $CH_2Cl_2$ and 250 mL 5% Acetone/$CH_2Cl_2$ to provide the title compound (116 mg) as a white solid (82%).

HRMS: calcd for $C_{11}H_{11}BrFNO$, 271.0008; found (ESI, [M+H]$^+$), 272.0088

Analytical HPLC: retention time 9.4 min, 210-370 nm, the Xterra® RP18 instrument, 3.5μ, 150×4.6 mm 40° C. 85/15-5/95 (Ammon. Form. Buff. pH=3.5/ACN+MeOH) for 10 min, hold 4 min 1.2 mL/min 5 μL injection.

C. 5-(7-fluoro-1,3,3-trimethyl-2-oxo-2,3-dihydro-1H-indol-5-yl)-1-methyl-1H-pyrrole-2-carbonitrile 5-Bromo-7-fluoro-1,3,3-trimethyl-1,3-dihydro-2H-indol-2-one (0.10 g, 0.36 mmol), 1-methyl-5-cyano-2-pyrroleboronic acid (95 mg, 0.63 mmol), KF (69 mg, 1.19 mmol) were suspended in 1 mL of dioxane. $Pd_2(dba)_3$ monochloroform adduct (3.1 mg, 0.003 mmol) and $Pd(P(t-Bu)_3)_2$ (4.6 mg, 0.009 mmol) were added and the mixture was stirred vigorously at 45° C. for 6 h. The mixture was diluted with 100 mL of EtOAc and filtered through a plug of silica gel and concentrated. Purification by flash chromatography (2% acetone/hexane) afforded the title compound (30 mg, 28%) as a tan solid.

HRMS: calcd for $C_{17}H_{16}FN_3O$, 297.1277; found (ESI, [M+H]$^+$), 298.1366

Analytical HPLC: retention time 9.4 min, 210-370 nm, the Xterra® RP18 instrument, 3.5μ, 150×4.6 mm 40° C. 85/15-5/95 (Ammon. Form. Buff. pH=3.5/ACN+MeOH) for 10 min, hold 4 min 1.2 mL/min 5 μL injection.

Example 5

5-(7-fluoro-3,3-dimethyl-2-oxo-2,3-dihydro-1H-indol-5-yl)-1H-pyrrole-2-carbonitrile A. tert-butyl 2-(7-fluoro-3,3-dimethyl-2-oxo-2,3-dihydro-1H-indol-5-yl)-1H-pyrrole-1-carboxylate A vial was charged with 5-bromo-7-fluoro-3,3-dimethyl-1,3-dihydro-2H-indol-2-one (1.0 g, 3.5 mmol), 1-tert-butoxycarbonyl-2-pyrroleboronic acid (1.12 g, 5.3 mmol), KF (0.67 g, 11.5 mmol), and $Pd_2(dba)_3$ monochloroform adduct (54 mg, 0.053 mmol) and placed under a nitrogen atmosphere. THF (8 mL) was added and the mixture was purged with nitrogen for 5 min. $P(t-Bu)_3$ (10% wt. solution in hexane 0.370 mL, 0.126 mmol) was added via syringe and the mixture was stirred at 25° C. for 16 h. The mixture was diluted with EtOAc and filtered through a plug of silica gel and concentrated. Purification by flash chromatography (500 mL 25% hexane/$CH_2Cl_2$ then 500 mL 100% $CH_2Cl_2$ then 500 mL 5% ethyl acetate/$CH_2Cl_2$) afforded the title compound (1.06 g, 88%) as colorless crystals.

HRMS: calcd for $C_{19}H_{21},FN_2O_3+H$, 345.16145; found (ESI, [M+H]$^+$), 345.1629.

Analytical HPLC: retention time 10.0 min, 210-370 nm, the Xterra® RP18 instrument, 3.5μ, 150×4.6 mm 40 C 85/15-5/95 (Ammon. Form. Buff. pH=3.5/ACN+MeOH) for 10 min, hold 4 min 1.2 mL/min 5 μL injection.

B. tert-butyl 2-cyano-5-(7-fluoro-3,3-dimethyl-2-oxo-2,3-dihydro-1H-indol-5-yl)-1H-pyrrole-1-carboxylate To a stirred solution of tert-butyl 2-(7-fluoro-3,3-dimethyl-2-oxo-2,3-dihydro-1H-indol-5-yl)-1H-pyrrole-1-carboxylate (1.0 g, 2.9 mmol) was added chlorosulfonylisocyanate (0.28 mL, 3.2 mmol). The mixture was stirred at 25° C. for 2 h then DMF (0.21 mL, 2.9 mmol) was added and the mixture was stirred for an additional 1 h. The mixture was diluted with ethyl acetate and washed with $NaHCO_3$, water, saturated aqueous NaCl, dried over $MgSO_4$, and concentrated. Flash chromatography (2% MeOH/$CH_2Cl_2$) afforded 0.23 g (21%) of the title compound as a white solid.

HRMS: calcd for $C_{20}H_{20}FN_3O_3$+H, 370.15670; found (ESI, [M+H]$^+$), 370.1554.
Analytical HPLC: retention time 9.5 min, 210-370 nm, the Xterra® RP18 instrument, 3.5µ, 150×4.6 mm 40° C. 85/15-5/95 (Ammon. Form. Buff. pH=3.5/ACN+MeOH) for 10 min, hold 4 min 1.2 mL/min 5 µL injection.

C. 5-(7-fluoro-3,3-dimethyl-2-oxo-2,3-dihydro-1H-indol-5-yl)-1H-pyrrole-2-carbonitrile tert-butyl 2-cyano-5-(7-fluoro-3,3-dimethyl-2-oxo-2,3-dihydro-1H-indol-5-yl)-1H-pyrrole-1-carboxylate (0.18 g, 0.50 mmol) was dissolved in 10 mL of dimethylacetamide and the solution was heated to 180° C. for 1 h. The mixture was cooled, diluted with ethyl acetate and washed with water, saturated aqueous NaCl, dried over MgSO$_4$, and concentrated. Flash chromatography (25% acetone/hexane) afforded 0.121 g (91%) of the title compound as a white solid.
HRMS: calcd for $C_{15}H_{12}FN_3O$+H, 270.10426; found (ESI, [M+H]$^+$), 270.1053.
Analytical HPLC: retention time 8.7 min, 210-370 nm, the Xterra® RP18 instrument, 3.5µ, 150×4.6 mm 40 C 85/15-5/95 (Ammon. Form. Buff. pH=3.5/ACN+MeOH) for 10 min, hold 4 min 1.2 mL/min 5 µL injection.

Example 6

General procedure for alkylation of 5-(7-fluoro-3,3-dimethyl-2-oxo-2,3-dihydro-1H-indol-5-yl)-1-methyl-1H-pyrrole-2-carbonitrile To a solution of 5-(7-fluoro-3,3-dimethyl-2-oxo-2,3-dihydro-1H-indol-5-yl)-1-methyl-1H-pyrrole-2-carbonitrile (0.10 g, 0.35 mmol) in dry THF (2 mL) was added potassium tert-butoxide (1 M solution in THF, 1 mL, 1 mmol). The mixture was stirred at room temperature for 1 hour. After this time, the appropriate alkylating agent (alkyl iodide or alkyl bromide) (0.5 mmol) was added by syringe. The resultant mixture was stirred overnight, then evaporated and subjected to purification by silica gel column chromatography (EtOAc/Hexane, gradient elution).
The compounds were characterized by high resolution mass spectrometry and HPLC. The HPLC conditions used were: the Xterra® RP18 column, 3.5µ, 150×4.6 mm, Flow Rate 1.2 mL/min, Mobile Phase Comp. 85/15-5/95 (Ammon. Form. Buff. pH=3.5/ACN+MeOH); Detection: 210-370 nm
The following compounds were prepared by this procedure:

A. methyl [5-(5-cyano-1-methyl-1H-pyrrol-2-yl)-7-fluoro-3,3-dimethyl-2-oxo-2,3-dihydro-1H-indol-1-yl]acetate Quantity obtained: 0.087 g
Alkylating agent: methyl bromoacetate (0.047 mL)
Analytical HPLC purity: 99.7%
Analytical HPLC retention time: 9.2 minutes
HRMS: calcd for $C_{19}H_{18}FN_3O_3$+H, 356.14050; found (ESI, [M+H]$^+$), 356.142

B. 5-(1-ethyl-7-fluoro-3,3-dimethyl-2-oxo-2,3-dihydro-1H-indol-5-yl)-1-methyl-1H-pyrrole-2-carbonitrile Quantity obtained: 0.0723 g
Alkylating agent: ethyl iodide (0.040 mL)
Analytical HPLC purity: 99.9%
Analytical HPLC retention time: 9.8 minutes.
HRMS: calcd for $C_{18}H_{18}FN_3O$+H, 312.15067; found (ESI, [M+H]$^+$), 312.1524; (delta=6 ppm)

C. 5-(7-fluoro-3,3-dimethyl-2-oxo-1-prop-2-yn-1-yl-2,3-dihydro-1H-indol-5-yl)-1-methyl-1H-pyrrole-2-carbonitrile Quantity obtained: 0.050 g
Alkylating agent: propargyl bromide (0.045 mL)
Analytical HPLC purity: 95.9%
Analytical HPLC retention time: 9.5 minutes
HRMS: calcd for $C_{19}H_{16}FN_3O$+H, 322.13502; found (ESI, [M+H]$^+$), 322.135

D. 5-[7-fluoro-3,3-dimethyl-2-oxo-1-(2-phenyl-ethyl)-2,3-dihydro-1H-indol-5-yl]-1-methyl-1H-pyrrole-2-carbonitrile Quantity obtained: 0.041 g
Alkylating agent: phenethyl bromide (0.067 mL)
Analytical HPLC purity: 100%
Analytical HPLC retention time: 10.8 minutes
HRMS: calcd for $C_{24}H_{22}FN_3O$+H, 388.18197; found (ESI, [M+H]$^+$), 388.1806

E. 5-(1-benzyl-7-fluoro-3,3-dimethyl-2-oxo-2,3-dihydro-1H-indol-5-yl)-1-methyl-1H-pyrrole-2-carbonitrile Quantity obtained: 0.0766 g
Alkylating agent: benzyl bromide (0.059 mL)
Analytical HPLC purity: 100%
Analytical HPLC retention time: 10.5 minutes
HRMS: calcd for $C_{23}H_{20}FN_3O$+H, 374.16632; found (ESI, [M+H]$^+$), 374.1685; (delta=6 ppm)

F. 5-(7-fluoro-3,3-dimethyl-2-oxo-1-propyl-2,3-dihydro-1H-indol-5-yl)-1-methyl-1H-pyrrole-2-carbonitrile Quantity obtained: 0.070 g
Alkylating agent: iodo propane (0.049 mL)
Analytical HPLC purity: 100%
Analytical HPLC retention time: 10.3 minutes
HRMS: calcd for $C_{19}H_{20}FN_3O$+H, 326.16632; found (ESI, [M+H]$^+$), 326.1652

G. 5-(7-fluoro-1-isobutyl-3,3-dimethyl-2-oxo-2,3-dihydro-1H-indol-5-yl)-1-methyl-1H-pyrrole-2-carbonitrile Quantity obtained: 0.0662 g
Alkylating agent: 2-methyliodopropane (0.060 mL)
Analytical HPLC purity: 100%
Analytical HPLC retention time: 10.6 minutes
HRMS: calcd for $C_{20}H_{22}FN_3O$+H, 340.18197; found (ESI, [M+H]$^+$), 340.1838

H. 5-(7-fluoro-1-isopropyl-3,3-dimethyl-2-oxo-2,3-dihydro-1H-indol-5-yl)-1-methyl-1H-pyrrole-2-carbonitrile Quantity obtained: 0.055 g
Alkylating agent: isopropyl iodide (0.049 mL)
Analytical HPLC purity: 98.8%
Analytical HPLC retention time: 10.3 minutes
HRMS: calcd for $C_{19}H_{20}FN_3O$+H, 326.16632; found (ESI, [M+H]$^+$), 326.1661

I. 5-(1-allyl-7-fluoro-3,3-dimethyl-2-oxo-2,3-dihydro-1H-indol-5-yl)-1-methyl-1H-pyrrole-2-carbonitrile Quantity obtained: 0.077 g
Alkylating agent: allyl iodide (0.045 mL)
Analytical HPLC purity: 99.6%
Analytical HPLC retention time: 9.9 minutes
HRMS: calcd for $C_{19}H_{18}FN_3O+H$, 324.15067; found (ESI, [M+H]$^+$), 324.1512

J. 5-(1-cyclohexyl-7-fluoro-3,3-dimethyl-2-oxo-2,3-dihydro-1H-indol-5-yl)-1-methyl-1H-pyrrole-2-carbonitrile Quantity obtained: 0.0037 g
Alkylating agent: cyclohexyl iodide (0.064 mL)
Analytical HPLC purity: 94.3%,
Analytical HPLC retention time: 11.2 minutes
HRMS: calcd for $C_{22}H_{24}FN_3O+H$, 366.19762; found (ESI, [M+H]$^+$), 366.1978

K. 5-(1-cyclopentyl-7-fluoro-3,3-dimethyl-2-oxo-2,3-dihydro-1H-indol-5-yl)-1-methyl-1H-pyrrole-2-carbonitrile Quantity obtained: 0.034 g
Alkylating agent: cyclopentyl iodide (0.057 mL)
Analytical HPLC purity: 100%
Analytical HPLC retention time: 10.9 minutes.
HRMS: calcd for $C_{21}H_{22}FN_3O+H$, 352.18197; found (ESI, [M+H]$^+$), 352.184; (delta=6 ppm)

Example 7

Pharmacology

Three type of assays are illustrated herein for use in assessing the activity of the compounds of the invention.

A. Effects of Progestins and Antiprogestins on Alkaline Phosphatase Activity in T47D Cells (T47D Alkaline Phosphatase Assay)

The molecules of the present invention are anticipated to be active in the antagonist mode in the T47D alkaline phosphatase assay at concentrations of 3 µM or lower.

1. Reagents:
Culture medium: DMEM:F12 (1:1) (GIBCO, BRL) supplemented with 5% (v/v) charcoal stripped fetal bovine serum (not heat-inactivated), 100 U/mL penicillin, 100 µg/mL streptomycin, and 2 mM GlutaMax (GIBCO, BRL).
Alkaline phosphatase assay buffer: I. 0.1M Tris-HCl, pH 9.8, containing 0.2% Triton X-100, 0.1M Tris-HCl, pH 9.8, containing 4 mM p-nitrophenyl phosphate (Sigma).

2. Cell Culture and Treatment:
Frozen T47D cells are thawed in a 37° C. water bath and diluted to 280,000 cells/mL in culture medium. To each well in a 96-well plate (Falcon, Becton Dickinson Labware), 180 µl of diluted cell suspension is added. Twenty µl of reference or test compounds diluted in the culture medium is then added to each well. When testing for progestin antagonist activity, reference antiprogestins or test compounds are added in the presence of 1 nM progesterone. The cells are incubated at 37° C. in a 5% $CO_2$ humidified atmosphere for 24 hours. For high throughput screening, one concentration of each compound will be tested at 0.3 µg/mL. Based on an average molecular weight of 300 g/mol for the compounds in the library, the concentration is approximately 1 µM.

Subsequently, active compounds will be tested in dose response assays to determine EC50 and IC50.

3. Alkaline Phosphatase Enzyme Assay:
At the end of treatment, the medium is removed from the plate. Fifty µl of assay buffer I is added to each well. The plates are shaken in a titer plate shaker for 15 min. Then 150 µl of assay buffer II is added to each well. Optical density measurements are taken at 5 min intervals for 30 min at a test wavelength of 405 nM.

4. Analysis of Dose-Response Data.
For reference and test compounds, a dose response curve is generated for dose vs. the rate of enzyme reaction (slope). Square root-transformed data are used for analysis of variance and nonlinear dose response curve fitting for both agonist and antagonist modes. Huber weighting is used to down-weight the effects of outliers. $EC_{50}$ or $IC_{50}$ values are calculated from the retransformed values. JMP software (SAS Institute, Inc.) is used for both one-way analysis of variance and non-4 linear dose response analysis in both single dose and dose response studies.

5. Reference Compounds:
Progesterone and trimegestone are reference progestins and RU486 is the reference antiprogestin. All reference compounds are run in full dose response curves and the $EC_{50}$ and $IC_{50}$ values are calculated.

| T47D Cell Alkaline Phosphatase Assay | |
|---|---|
| Chemical Name | $IC_{50}$ (nM) |
| 5-(7'-fluoro-2'-oxo-1',2'-dihydrospiro[cyclobutane-1,3'-indol]-5'-yl)-1-methyl-1H-pyrrole-2-carbonitrile | 2.75 |
| 5-(4-fluoro-3,3-dimethyl-2-oxo-2,3-dihydro-1H-indol-5-yl)-1-methyl-1H-pyrrole-2-carbonitrile | 30 |
| 5-(7-fluoro-3,3-dimethyl-2-oxo-2,3-dihydro-1H-indol-5-yl)-1-methyl-1H-pyrrole-2-carbonitrile | 5.4 |
| 5-(7-fluoro-2-oxo-2,3-dihydro-1H-indol-5-yl)-1-methyl-1H-pyrrole-2-carbonitrile | 109 |
| 5-(7-fluoro-2-oxo-1,3,3-trimethyl-2-oxo-2,3-dihydro-1H-indol-5-yl)-1-methyl-1H-pyrrole-2-carbonitrile | 22.3 |
| 5-(7'-fluoro-2'-oxo-1',2'-dihydrospiro[cyclopropane-1,3'-indol]-5'-yl)-1-methyl-1H-pyrrole-2-carbonitrile | 10.8 |
| 5-(3,3-diethyl-7-fluoro-2-oxo-2,3-dihydro-1H-indol-5-yl)-1-methyl-1H-pyrrole-2-carbonitrile | 4.95 |
| 5-(7'-fluoro-2'-oxo-1',2'-dihydrospiro[cyclopentane-1,3'-indol]-5'-yl)-1-methyl-1H-pyrrole-2-carbonitrile | 3.2 |
| tert-butyl-2-cyano-5-(7-fluoro-3,3-dimethyl-2-oxo-2,3-dihydro-1H-indol-5-yl)-1H-pyrrole-1-carboxylate | 125 |
| 5-(7-fluoro-3,3-dimethyl-2-oxo-2,3-dihydro-1H-indol-5-yl)-1H-pyrrole-2-carbonitrile | 107 |
| 5-(4'-fluoro-2'-oxo-1',2'-dihydrospiro[cyclopropane-1,3'-indol]-5'yl)-1-methyl-1H-pyrrole-2-carbonitrile | 7.8 |
| Methyl-[5-(5-cyano-1-methyl-1H-pyrrol-2-yl)-7-fluoro-3,3-dimethyl-2-oxo-2,3-dihydro-1H-indol-1-yl] acetate | 48 |
| 5-(1-ethyl-7-fluoro-3,3-dimethyl-2-oxo-2,3-dihydro-1H-indol-5-yl)-1-methyl-1H-pyrrole-2-carbonitrile | 29.5 |
| 5-(7-fluoro-3,3-dimethyl-2-oxo-1-prop-2-yn-1-yl-2,3-dihydro-1H-indol-5-yl)-1-methyl-1H-pyrrole-2-carbonitrile | 30 |
| 5-[7-fluoro-3,3-dimethyl-2-oxo-1(2-phenylethyl)-2,3-dihydro-1H-indol-5-yl]-1-methyl-1H-pyrrole-2-carbonitrile | 350.7 |
| 5-(1-benzyl-7-fluoro-3,3-dimethyl-2-oxo-2,3-dihydro-1H-indol-5-yl)-1-methyl-1H-pyrrole-2-carbonitrile | 164.3 |
| 5-(7-fluoro-3,3-dimethyl-2-oxo-1-propyl-2,3-dihydro-1H-indol-5-yl)-1-methyl-1H-pyrrole-2-carbonitrile | 26.5 |
| 5-(7-fluoro-1-isobutyl-3,3-dimethyl-2-oxo-2,3-dihydro-1H-indol-5-yl)-1-methyl-1H-pyrrole-2-carbonitrile | 29.9 |
| 5-(7-fluoro-1-isopropyl-3,3-dimethyl-2-oxo-2,3-dihydro-1H-indol-5-yl)-1-methyl-1H-pyrrole-2-carbonitrile | 13 |
| 5-(1-allyl-7-fluoro-3,3-dimethyl-2-oxo-2,3-dihydro-1H-indol-5-yl)-1-methyl-1H-pyrrole-2-carbonitrile | 4.5 |
| 5-(1-cyclohexyl-7-fluoro-3,3-dimethyl-2-oxo-2,3-dihydro-1H-indol-5-yl)-1-methyl-1H-pyrrole-2-carbonitrile | 193.9 |
| 5-(1-cyclopentyl-7-fluoro-3,3-dimethyl-2-oxo-2,3-dihydro-1H-indol-5-yl)-1-methyl-1H-pyrrole-2-carbonitrile | 25.2 |

B. Progestational and Antiprogestational Activity in Mature Ovariectomized Rats (Rat Decidualization Assay)

This assay is used to evaluate the effect of progestins and antiprogestins on rat uterine decidualization and compare the relative potencies of various test compounds.

1. Methods and Reagents

Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response is found when these two vehicles are compared.

2. Animals

Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

3. Treatment

Rats are weighed and randomly assigned to groups of 4 or 5 before treatment. Test compounds in 0.2 mL vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the entire treatment period. One group of animals receiving an $EC_{50}$ dose of progesterone alone serves as a positive control.

4. Dosing

Doses are prepared based upon mg/kg mean group body weight. In all studies, a control group receiving vehicle is included. Determination of dose response curves is carried out using doses with half log increases (e.g. 0.1, 0.3, 1.0, 3.0 mg/kg).

5. Decidual Induction

Approximately 24 hr after the third injection, decidualization is induced in one of the uterine horns of anesthetized rats by scratching the antimesometrial luminal epithelium with a blunt 21 G needle. The contralateral horn is not scratched and serves as an unstimulated control. Approximately 24 hr following the final treatment, rats are sacrificed by CO asphyxiation and bodyweight measured. Uteri are removed and trimmed of fat. Decidualized (D-horn) and control (C-horn) uterine horns are weighed separately.

6. Analysis of Results

In agonist mode, the increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance (ANOVA). $EC_{50}$ is calculated from the transformed value. In antagonist mode, a square root transformation on raw responses (D-horn/C-horn) is recommended by using maximum likelihood Box-Cox transformation. The Huber weight is used to down weight the outlying transformed observations for dose-response curve fitting and one-way ANOVA. $IC_{50}$ is calculated from the retransformed value. JMP software (SAS Institute, Inc.) is used for both one-way ANOVA and non-linear dose-response analyses.

7. Reference Compounds

All progestin or antiprogestin reference compounds are run in full dose-response curves and the $EC_{50}$ or $IC_{50}$ for decidual response is calculated.

C. Cynomolgus Monkey Menses Induction

1. Experimental Design

The effects of administered compound(s) in either a single dose or a dose-response paradigm versus an appropriate control (vehicle alone) are determined. When a compound is tested at a single dose, a group of four animals will be used for the dose. In the dose response study, each experiment will involve up to 5 groups of animals (a control group and 4 groups of animals treated with varying doses of the compound). Experimental groups will contain 3-4 animals/group, since this sample size is commonly used in the literature and has been found appropriate based on our own experience. The animals are treated with test compounds once or twice daily for 4 days in the mid-luteal phase of the menstrual cycle to assess the efficacy of the compounds on the reproductive parameters menstruation.

2. Procedures

Initially, animals are characterized in terms of their reproductive cyclicity by observing time of menstruation. Only those animals with two consecutive normal cycles are used to evaluate test compounds. Menses will be determined by daily gross examination for vaginal bleeding.

In each experiment, animals will be treated once or twice daily IV, IM, SC or PO with the test compound. Appropriate vehicles will be determined for each route of administration and will be specified through protocol amendments. The po vehicle will be 2% Tween-80 or 2% Tween-80 in 0.5% aqueous methylcellulose. Control animals will be treated with the vehicle alone. Maximum dose volumes to be used are as follows: gavage 10 mL/Kg, IV 10 mL/Kg, SC 1.5 mL/Kg, IM 0.2 mL/Kg. Efficacy will be defined as induction of early menstruation for contraceptive compounds.

3. COMPARATIVE EXAMPLE 5-(3,3-Dimethyl-2-oxo-2,3-dihydro-1H-indol-5-yl)-1-methyl-1H-pyrrole-2-carbonitrile is a PR antagonist in the alkaline phosphatase assay ($IC_{50}$=10 nM) and is very potent in the rat decidual assay ($ED_{50}$=0.2 mg/k po). However it was not active at a dose of 5 mg/kg po in the cynomolgus monkey menses induction assay (the compound was not dosed higher than 5 mg/kg). 5-(7-fluoro-3,3-dimethyl-2-oxo-2,3-dihydro-1H-indol-5-yl)-1-methyl-1H-pyrrole-2-carbonitrile was also active in the T47D alkaline phosphase assay ($IC_{50}$=3.4 nM) and in the rat decidual assay ($ED_{50}$=0.1 mg/kg po). However, in the cynomolgus monkey menses induction assay, described above, it induced an early onset of menses in 4 out of 5 animals dosed at 5 mg/kg po.

When cynomolgus monkeys were dosed with 5-(3,3-dimethyl-2-oxo-2,3-dihydro-1H-indol-5-yl)-1-methyl-1H-pyrrole-2-carbonitrile or 5-(7-fluoro-3,3-dimethyl-2-oxo-2,3-dihydro-1H-indol-5-yl)-1-methyl-1H-pyrrole-2-carbonitrile intravenously at 0.25 mg/kg, the following key pharmacokinetic parameters were measured: for 5-(3,3-dimethyl-2-oxo-2,3-dihydro-1H-indol-5-yl)-1-methyl-1H-pyrrole-2-carbonitrile the mean half life ($t_{1/2}$) observed in the animals was 2.1 hours, and the exposure ($AUC_{0-\infty}$) was 343 ng*hr/mL. For 5-(7-fluoro-3,3-dimethyl-2-oxo-2,3-dihydro-1H-indol-5-yl)-1-methyl-1H-pyrrole-2-carbonitrile (0.25 mg/kg i.v.) the mean half life ($t_{1/2}$) observed in the animals was 8.8 hours, and the exposure ($AUC_{0-\infty}$) was 578 ng*hr/mL. Therefore from the preceding data it is clear that the $R_6$=fluorine group present in 5-(7-fluoro-3,3-dimethyl-2-oxo-2,3-dihydro-1H-indol-5-yl)-1-methyl-1H-pyrrole-2-carbonitrile dramatically improves the pharmacokinetic performance of the molecule. This improved pharmacokinetic performance translates in the cynomolgus menses induction assay to a dramatic improvement in activity.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A compound of formula I:

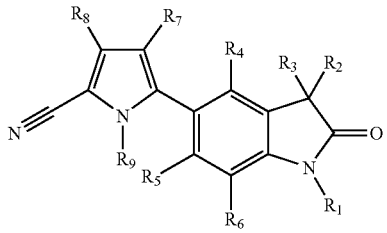

wherein,
R₁ is hydrogen, alkyl, substituted alkyl, cycloalkyl, $C_3$ to $C_6$ alkenyl, or $C_3$ to $C_6$ alkynyl;
R₂ and R₃ are each independently selected from the group consisting of hydrogen, $C_1$ to $C_2$ alkyl, and substituted $C_1$ to $C_2$ alkyl; or
R₂ and R₃ are taken together to form a ring and together contain —$CH_2$—$(CH_2)_n$—$CH_2$—;
n is 0 or 1;
R₄ is fluorine;
R₅ is hydrogen;
R₆ is hydrogen or halogen;
R₇ is hydrogen, alkyl, or halogen;
R₈ is hydrogen;
R₉ is hydrogen, alkyl, substituted alkyl, or $COOR^A$;
$R^A$ is alkyl or substituted alkyl;
or a pharmaceutically acceptable salt thereof.

2. The compound according to claim 1, wherein
R₁ is hydrogen or alkyl;
R₂ and R₃ are taken together to form a ring and together contain —$CH_2$—$(CH_2)_n$—$CH_2$—;
n is 1.

3. The compound according to claim 1, wherein R₂ or R₃ is methyl or ethyl.

4. The compound according to claim 1, wherein:
R₁ is hydrogen;
R₂ and R₃ are $C_1$ to $C_2$ alkyl;
R₆ is fluorine;
R₇ is hydrogen; and
R₉ is alkyl.

5. The compound according to claim 1, wherein R₉ is methyl or $COOR^A$ and $R^A$ is tert-butyl.

6. The compound according to claim 1, wherein said compound is 5-(4-fluoro-3,3-dimethyl-2-oxo-2,3-dihydro-1H-indol-5-yl)-1-methyl-1H-pyrrole-2-carbonitrile.

7. A pharmaceutical composition comprising a compound of claim 1, or a pharmaceutically acceptable salt thereof, and a pharmaceutically carrier or excipient.

8. A pharmaceutically useful kit adapted for daily oral administration which comprises:
(a) a first phase of from 14 to 21 daily dosage units of a progestational agent equal in progestational activity to about 35 to about 150 μg levonorgestrel;
(b) a second phase of from 1 to 11 daily dosage units of a compound of claim 1, each daily dosage unit containing said compound at a daily dosage of from about 2 to 50 mg; and
(c) a third phase of daily dosage units of an orally and pharmaceutically acceptable placebo;
wherein the total number of the daily dosage units in the first phase, second phase and third phase equals 28.

9. A method for preparing a compound of claim 1 comprising:
(a) alkylating an optionally substituted oxindole;
(b) brominating the product of step (a); and
(c) coupling the product of step (b) with a 2-cyanopyrrole.

10. The method according to claim 9, wherein said optionally substituted oxindole is of the structure:

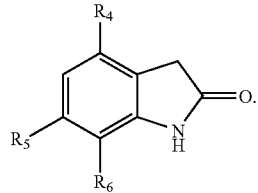

11. The method according to claim 9, wherein the product of step (a) is of the structure:

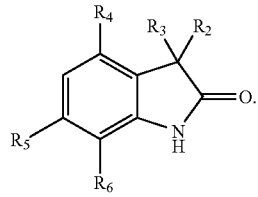

12. The method according to claim 9, wherein the product of step (b) is of the structure:

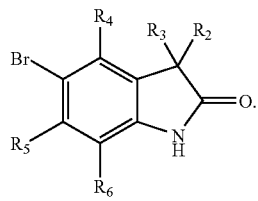

13. The method according to claim 9, wherein said cyanopyrrole is of the structure:

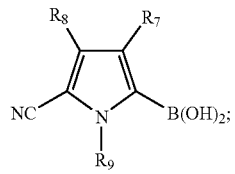

or said cyanopyrrole is the product of the reaction of lithium diisopropylamide, a tri-alkylborate, and a pyrrole of the following structure:

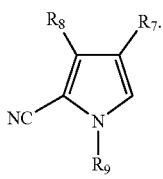

14. A method for preparing a compound of claim 1 comprising:
(a) coupling a 5-bromo substituted oxindole and a pyrrole boronic acid containing a protecting group;
(b) converting the product of step a) to the nitrile; and
(c) removing said protecting group from the product of step b).

15. The method according to claim 14, wherein said 5-bromo substituted oxindole is of the structure:

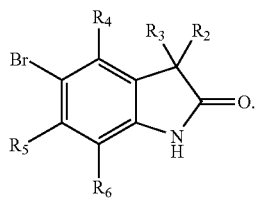

16. The method according to claim 14, wherein said pyrrole boronic acid is of the structure:

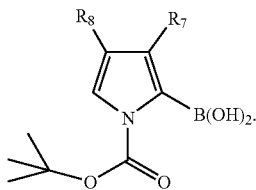

17. The method according to claim 14, wherein the product of step (b) is of the structure:

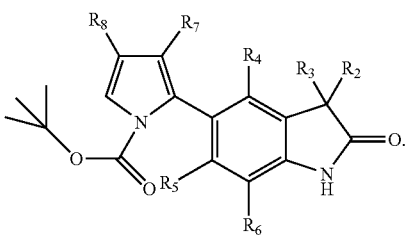

18. A method for preparing a compound of claim 1, comprising:
(a) alkylating an optionally substituted oxindole of the structure:

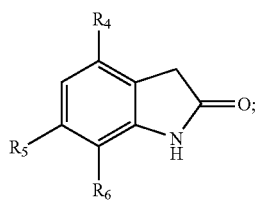

(b) brominating the product of step a) to form a compound of the structure:

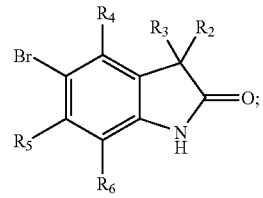

and
(c) coupling the product of step b) with a 2-cyanopyrrole of the structure:

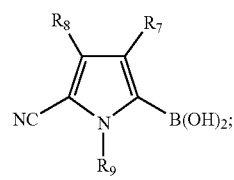

said cyanopyrrole is the product of the reaction of lithium diisopropylamide, a tri-alkylborate, and a pyrrole of the following structure:

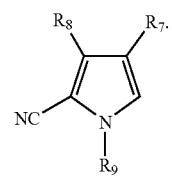

19. The compound according to claim 1 which is 5-(4'-fluoro-2'-oxo-1',2'-dihydrospiro[cyclopropane-1,3'-indol]-5'yl)-1-methyl-1H-pyrrole-2-carbonitrile.

20. A compound of formula I:

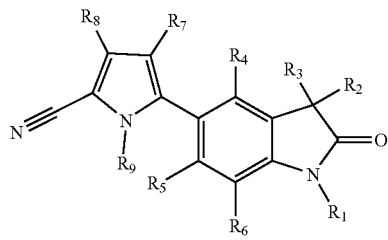

wherein,
$R_1$ is hydrogen, alkyl, substituted alkyl, cycloalkyl, $C_3$ to $C_6$ alkenyl, or $C_3$ to $C_6$ alkynyl;
$R_2$ and $R_3$ are each independently selected from the group consisting of hydrogen, $C_1$ to $C_2$ alkyl, and substituted $C_1$ to $C_2$ alkyl; or
$R_2$ and $R_3$ are taken together to form a ring and together contain —$CH_2$—$(CH_2)_n$—$CH_2$—;
n is 0 or 1;
$R_4$ is hydrogen or halogen;
$R_5$ is hydrogen;
$R_6$ is hydrogen or halogen;
$R_7$ is hydrogen, alkyl, or halogen;
$R_8$ is hydrogen;
$R_9$ is hydrogen, alkyl, substituted alkyl, or $COOR^4$;
$R^A$ is alkyl or substituted alkyl;
or a pharmaceutically acceptable salt thereof.

21. The compound according to claim 20, wherein said compound is selected from the group consisting of 5-(7'-fluoro-2'-oxo-1',2'-dihydrospiro[cyclobutane-1,3'-indol]-5'-yl)-1-methyl-1H-pyrrole-2-carbonitrile; 5-(7-fluoro-2-oxo-2,3-dihydro-1H-indol-5-yl)-1-methyl-1H-pyrrole-2-carbonitrile; 5-(7-fluoro-2-oxo-1,3,3-trimethyl-2-oxo-2,3-dihydro-1H-indol-5-yl)-1-methyl-1H-pyrrole-2-carbonitrile; and 5-(3,3-diethyl-7-fluoro-2-oxo-2,3-dihydro-1H-indol-5-yl)-1-methyl-1H-pyrrole-2-carbonitrile.

22. The compound according to claim 20, wherein
$R_1$ is hydrogen or alkyl;
$R_2$ and $R_3$ are taken together to form a ring and together contain —$CH_2$—($CH_2$)$_n$—$CH_2$—;
n is 1.

23. The compound according to claim 20, wherein $R_2$ or $R_3$ is methyl or ethyl.

24. The compound according to claim 20, wherein $R_9$ is methyl or $COOR^A$ and $R^A$ is tert-butyl.

25. The compound according to claim 20, wherein said compound is selected from the group consisting of 5-(7-fluoro-3,3-dimethyl-2-oxo-2,3-dihydro-1H-indol-5-yl)-1-methyl-1H-pyrrole-2-carbonitrile; 5-(7'-fluoro-2'-oxo-1',2'-dihydrospiro[cyclopropane-1,3'-indol]-5'-yl)-1-methyl-1H-pyrrole-2-carbonitrile; 5-(7-fluoro-1,3,3-trimethyl-2-oxo-2,3-dihydro-1H-indol-5-yl)-1-methyl-1H-pyrrole-2-carbonitrile; tert-butyl 2-(7-fluoro-3,3-dimethyl-2-oxo-2,3-dihydro-1H-indol-5-yl)-1H-pyrrole-1-carboxylate; tert-butyl 2-cyano-5-(7-fluoro-3,3-dimethyl-2-oxo-2,3-dihydro-1H-indol-5-yl)-1H-pyrrole-1-carboxylate; 5-(7-fluoro-3,3-dimethyl-2-oxo-2,3-dihydro-1H-indol-5-yl)-1H-pyrrole-2-carbonitrile; Methyl-[5-(5-cyano-1-methyl-1H-pyrrole-2-yl)-7-fluoro-3,3-dimethyl-2-oxo-2,3-dihydro-1H-indol-1-yl]acetate; 5-(1-ethyl-7-fluoro-3,3-dimethyl-2-oxo-2,3-dihydro-1H-indol-5-yl)-1-methyl-1H-pyrrole-2-carbonitrile; 5-(7-fluoro-3,3-dimethyl-2-oxo-1-prop-2-yn-1-yl-2,3-dihydro-1H-indol-5-yl)-1-methyl-1H-pyrrole-2-carbonitrile; 5-[7-fluoro-3,3-dimethyl-2-oxo-1-(2-phenylethyl)-2,3-dihydro-1H-indol-5-yl]-1-methyl-1H-pyrrole-2-carbonitrile; 5-(1-benzyl-7-fluoro-3,3-dimethyl-2-oxo-2,3-dihydro-1H-indol-5-yl)-1-methyl-1H-pyrrole-2-carbonitrile; 5-(7-fluoro-3,3-dimethyl-2-oxo-1-propyl-2,3-dihydro-1H-indol-5-yl)-1-methyl-1H-pyrrole-2-carbonitrile; 5-(7-fluoro-1-isobutyl-3,3-dimethyl-2-oxo-2,3-dihydro-1H-indol-5-yl)-1-methyl-1H-pyrrole-2-carbonitrile; 5-(7-fluoro-1-isopropyl-3,3-dimethyl-2-oxo-2,3-dihydro-1H-indol-5-yl)-1-methyl-1H-pyrrole-2-carbonitrile; 5-(1-allyl-7-fluoro-3,3-dimethyl-2-oxo-2,3-dihydro-1H-indol-5-yl)-1-methyl-1H-pyrrole-2-carbonitrile; 5-(1-cyclohexyl-7-fluoro-3,3-dimethyl-2-oxo-2,3-dihydro-1H-indol-5-yl)-1-methyl-1H-pyrrole-2-carbonitrile; 5-(1-cyclopentyl-7-fluoro-3,3-dimethyl-2-oxo-2,3-dihydro-1H-indol-5-yl)-1-methyl-1H-pyrrole-2-carbonitrile.

26. A pharmaceutical composition comprising a compound of claim 20, or a pharmaceutically acceptable salt thereof, and a pharmaceutically acceptable carrier or excipient.

27. A pharmaceutically useful kit adapted for daily oral administration which comprises:
(a) a first phase of from 14 to 21 daily dosage units of a progestational agent equal in progestational activity to about 35 to about 150 μg levonorgestrel;
(b) a second phase of from 1 to 11 daily dosage units of a compound of claim 20, each daily dosage unit containing said compound at a daily dosage of from about 2 to 50 mg; and
(c) a third phase of daily dosage units of an orally and pharmaceutically acceptable placebo;
wherein the total number of the daily dosage units in the first phase, second phase and third phase equals 28.

28. A method for preparing a compound of claim 20, comprising:
(a) alkylating an optionally substituted oxindole;
(b) brominating the product of step (a); and
(c) coupling the product of step (b) with a 2-cyanopyrrole.

29. The method according to claim 28, wherein said optionally substituted oxindole is of the structure:

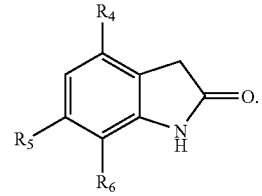

30. The method according to claim 28, wherein the product of step (a) is of the structure:

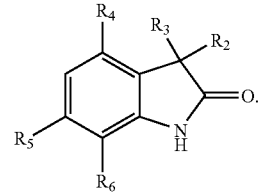

31. The method according to claim 28, wherein the product of step (b) is of the structure:

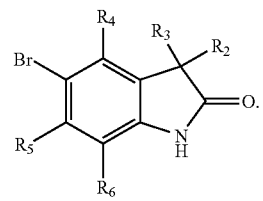

32. The method according to claim 28, wherein said cyanopyrrole is of the structure:

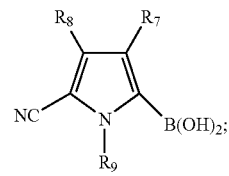

or
said cyanopyrrole is the product of the reaction of lithium diisopropylamide, a tri-alkylborate, and a pyrrole of the following structure:

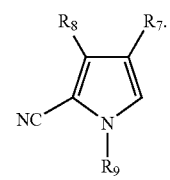

33. A method for preparing a compound of claim 20, comprising:
(a) coupling a 5-bromo substituted oxindole and a pyrrole boronic acid containing a protecting group;
(b) converting the product of step a) to the nitrile; and (c) removing said protecting group from the product of step b).

34. The method according to claim 33, wherein said 5-bromo substituted oxindole is of the structure:

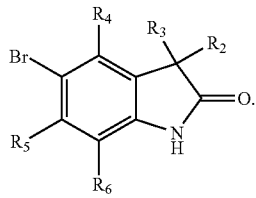

35. The method according to claim 33, wherein said pyrrole boronic acid is of the structure:

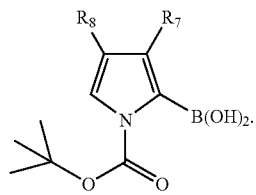

36. The method according to claim 33, wherein the product of step (b) is of the structure:

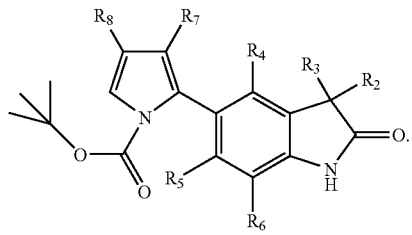

37. A method for preparing a compound of claim 20, comprising:

(a) alkylating an optionally substituted oxindole of the structure:

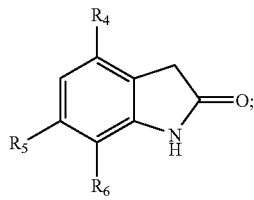

(b) brominating the product of step a) to form a compound of the structure:

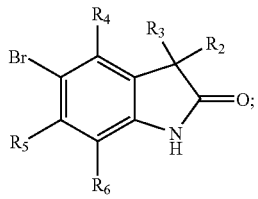

and (c) coupling the product of step b) with a 2-cyanopyrrole of the structure:

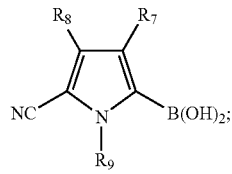

said cyanopyrrole is the product of the reaction of lithium diisopropylamide, a tri-alkylborate, and a pyrrole of the following structure:

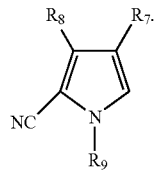

* * * * *

UNITED STATES PATENT AND TRADEMARK OFFICE
CERTIFICATE OF CORRECTION

PATENT NO. : 7,317,037 B2
APPLICATION NO. : 11/175824
DATED : January 8, 2008
INVENTOR(S) : A. Fensome et al.

Page 1 of 1

It is certified that error appears in the above-identified patent and that said Letters Patent is hereby corrected as shown below:

Claim 20, line 61, replace "hydrogen or halogen" with --fluorine--.

Signed and Sealed this

Twentieth Day of October, 2009

David J. Kappos
*Director of the United States Patent and Trademark Office*

UNITED STATES PATENT AND TRADEMARK OFFICE
CERTIFICATE OF CORRECTION

PATENT NO.         : 7,317,037 B2
APPLICATION NO.   : 11/175824
DATED             : January 8, 2008
INVENTOR(S)       : A. Fensome et al.

Page 1 of 1

It is certified that error appears in the above-identified patent and that said Letters Patent is hereby corrected as shown below:

Column 32, Claim 20, line 61, replace "hydrogen or halogen" with --fluorine--.

This certificate supersedes the Certificate of Correction issued October 20, 2009.

Signed and Sealed this

Tenth Day of November, 2009

David J. Kappos
*Director of the United States Patent and Trademark Office*